United States Patent
Bernard et al.

(10) Patent No.: US 6,459,001 B1
(45) Date of Patent: Oct. 1, 2002

(54) TRICYCLIC COMPOUNDS, THEIR PREPARATION PROCESS AND THE INTERMEDIATES OF THIS PROCESS, THEIR USE AS MEDICAMENTS AND THE PHARMACEUTICAL COMPOSITIONS CONTAINING THEM

(75) Inventors: Serge Bernard, Le Plessis Belleville; Denis Carniato, Marcoussis; Jean-Francois Gourvest, Claye-Souilly; Jean-Georges Teutsch, Pantin, all of (FR); Jochen Knolle, Kriftel (DE); Hans-Ulrich Stilz, Frankfurt am Main (DE); Volkmar Wehner, Sandberg (DE); Sarah C. Bodary, San Bruno, CA (US); Thomas R. Gadek, Oakland, CA (US); Robert S. McDowell, San Francisco, CA (US); Robert M. Pitti, El Cerrito, CA (US)

(73) Assignees: Aventis Pharma S.A. (FR); Genetech

( * ) Notice: Subject to any disclaimer, the term of this patent is extended or adjusted under 35 U.S.C. 154(b) by 0 days.

(21) Appl. No.: 09/769,018

(22) Filed: Jan. 25, 2001

Related U.S. Application Data

(62) Division of application No. 09/155,063, filed as application No. PCT/FR97/00487 on Mar. 20, 1997, now Pat. No. 6,221,907.

(51) Int. Cl.[7] .................. C07C 251/82; C07C 281/06
(52) U.S. Cl. .................. 568/326; 560/34; 562/439; 564/20; 564/21; 564/36; 564/81; 564/163
(58) Field of Search .................. 568/326; 560/34; 564/20, 21, 36, 81, 163; 562/439

(56) References Cited

U.S. PATENT DOCUMENTS 5,705,704 * 1/1998 Brion et al. .................. 568/326

* cited by examiner

Primary Examiner—Mukund J. Shah
Assistant Examiner—Venkataraman Balasubrasubramanian
(74) Attorney, Agent, or Firm—Bierman, Muserlian and Lucas

(57) ABSTRACT

The subject of the invention is the products of formula (I):

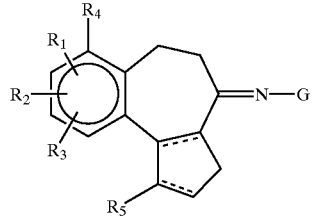

in which $R_1$, $R_2$, $R_3$, $R_4$, $R_5$ and G are as defined in the description, the dotted lines represent an optional second bond, as well as the addition salts with acids and bases and the esters, their preparation process and the intermediates of this process, their use as medicines and the pharmaceutical compositions containing them.

6 Claims, No Drawings

TRICYCLIC COMPOUNDS, THEIR PREPARATION PROCESS AND THE INTERMEDIATES OF THIS PROCESS, THEIR USE AS MEDICAMENTS AND THE PHARMACEUTICAL COMPOSITIONS CONTAINING THEM

PRIOR APPLICATIONS

This application is a division of U.S. patent application Ser. No. 09/155,063 filed Feb. 2, 1999, now U.S. Pat. No. 6,221,907 which is a 371 of PCT/FR97/00487 filed Mar. 20, 1997.

The present invention relates to new tricyclic compounds, their preparation process and the intermediates of this process, their use as medicaments and the pharmaceutical compositions containing them.

A subject of the present invention is the compounds of general formula (I):

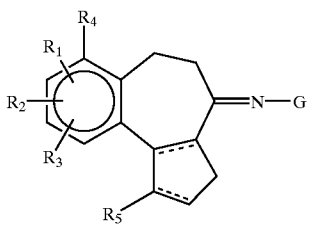

(I)

in which $R_1$ represents a —C≡C—[A]—[B]—$COR_6$, —CH=CH—[A]—[B]—$COR_6$, —$(CH_2)_2$—[A]—[B]—$COR_6$, —O—[A]—[B]—$COR_6$, —$CH_2CO$—[A]—[B]—$COR_6$ group, —[A]— representing either a bivalent hydrocarbonated radical derived from a saturated or unsaturated, linear or branched structure containing 1 to 12 carbon atoms and 1 to 6 heteroatoms chosen from oxygen, nitrogen or sulphur atoms, or a bivalent radical derived from a saturated or unsaturated, linear or branched acyclic hydrocarbon containing 1 to 12 carbon atoms,

[B] representing a phenyl radical, a CH[Z] radical, or a single bond,

Z represents a hydrogen atom, one of the following groups:
$(D)_{0-6}$—NRaRb, $(D)_{0-6}$—NH—$SO_2$—Rc, $(D)_{0-6}$—NH—$CO_2$—Rc, $(D)_{0-6}$—NH—CO—Rc, $(D)_{0-6}$—NH—$SO_2$—NH—Rc, $(D)_{0-6}$—NH—CO—NH—Rc, $(D)_{0-6}$—$CO_2$—Rc, $(D)_{0-6}$—$SO_2$—Rc, $(D)_{0-6}$—CO—Rc or $(D)_{0-6}$—Rc in which $(D)_{0-6}$ is a bivalent radical derived from a saturated or unsaturated, linear or branched acyclic hydrocarbon containing 0 to 6 carbon atoms, Ra, Rb and Rc represent a hydrogen atom, a $(CH_2)_{0-3}$—Ar radical in which Ar represents a carbocyclic aryl group containing 6 to 18 carbon atoms, a $(CH_2)_{0-3}$-Het radical in which Het represents a radical derived from a saturated or unsaturated, aromatic or non-aromatic heterocycle containing 1 to 9 carbon atoms and 1 to 5 heteroatoms chosen from oxygen, nitrogen or sulphur atoms, a $(CH_2)_{0-3}$-Alk radical in which Alk represents a radical derived from a saturated or unsaturated, linear, branched or cyclic, non-aromatic hydrocarbon, containing 1 to 12 carbon atoms, the Het, Ar and Alk radicals being able to be non-substituted or substituted, or also, Ra and Rb represent together with the nitrogen atom to which they are linked a saturated or unsaturated, aromatic or non-aromatic, nitrogenous heterocycle optionally containing one or more heteroatoms chosen from oxygen, nitrogen or sulphur atoms, this radical being able to be substituted or non-substituted, $R_6$ represents a hydroxyl radical, an O-Alk O—Ar, $NH_2$ NH-Alk, $N(Alk)^2$ radical or the remainder of a L or D amino acid, Alk and Ar being as defined previously and being optionally substituted or not substituted, $R_2$ and $R_3$, identical or different, represent either a hydrogen atom, a hydroxyl radical, an O-Alk radical or an O—$(CH_2)_{0-3}$—Ar radical, Alk and Ar being as defined previously, or $R_2$ and $R_3$ form together with a ring of —O—$(CRdRe)_n$— type, n being an integer from 1 to 5, Rd and Re independently of each other represent a hydrogen atom, an alkyl radical containing 1 to 6 carbon atoms, or a phenyl radical, $R_4$ represents a hydrogen atom, a halogen atom, one of the following groups: hydroxyl, amino, nitro, cyano, $CF_3$, acyl or acyloxy containing 1 to 12 carbon atoms, alkyl, alkenyl, alkynyl, alkylthio, alkoxy, alkylamino, dialkylamino, dialkylaminoalkyl, dialkylaminoalkyloxy, in which the term alkyl contains 1 to 6 carbon atoms, $R_5$ represents a hydrogen atom, a hydroxyl radical, a halogen atom, an O-Alk radical or an O—$(CH_2)_{0-3}$—Ar radical, Alk and Ar being as defined previously, G represents,
either a radical of formula G1

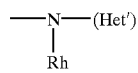

in which Rh is a hydrogen atom or an (Alk) group as defined previously and (Het') is a heterocycle of general formula:

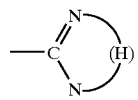

in which (H) forms, with the N=C—NH— unit, the remainder of a saturated or unsaturated, mono- or bicyclic, aromatic or non-aromatic heterocycle containing 1 to 9 carbon atoms and 2 to 5 heteroatoms chosen from oxygen, nitrogen and sulphur atoms, this radical being able to be substituted or non-substituted, or an NRaRb radical (radical G2), Ra and Rb being as defined above, or a (Het) radical (radical G3) as defined above, or an —NRh—C(=X)—NHRc radical (radical G4), in which X is a sulphur or oxygen atom or NH, Rh and Rc are as defined previously, or an —NRh—$SO_2$Rc radical, (radical G5), in which Rh and Rc are as defined previously, the dotted lines represent an optional second bond, as well as the addition salts with acids and bases and the esters. $R_1$, $R_2$ and $R_3$ can be in position 8, 9 or 10 of the tricycle.

By compound of formula (I) is meant all the possible geometrical isomers and stereoisomers taken individually or as a mixture.

By —[A]— group representing a bivalent radical derived from a saturated or unsaturated, linear or branched structure containing 1 to 12 carbon atoms and 1 to 6 heteroatoms chosen from oxygen, nitrogen and sulphur atoms, is meant in particular, radicals derived from the alkanes some of whose carbons are replaced by oxygen or sulphur atoms, or by the following groups: C=O, SO, SO$_2$, NH, N(Alk), NH—CO, N(Alk)—CO, CO—NH, CO—N(Alk), SO$_2$—NH, SO$_2$—N(Alk), (Alk) being as defined above. It can therefore be the following radicals:

—CH$_2$—CH$_2$—O—CH$_2$—CH$_2$—, —CH$_2$—CH$_2$—N(CH$_3$)—CH$_2$—CH$_2$—, CH$_2$—CH$_2$—C(O)—CH$_2$—CH$_2$, CH$_2$—C(O)—C(Me)$_2$—CH$_2$.

When —[A]— represents a bivalent radical derived from a saturated or unsaturated, linear or branched, acyclic hydrocarbon containing 1 to 12 carbon atoms, there are meant in particular the alkylene radicals of formula —(CH$_2$)$_n$—, in which n represents an integer comprised between 1 and 12, such as —CH$_2$—, —CH$_2$CH$_2$—, —CH$_2$CH$_2$CH$_2$—, or the alkenylene or alkynylene radicals such as —CH=CH—CH$_2$— or —C≡C—CH$_2$—.

When these bivalent radicals are branched, they can be radicals such as —CH(CH$_3$)—; —C(Me)$_2$, —CH$_2$—C(Me)$_2$—, —CH(Et)—, —CH(C=CH)— or —C(C≡CH)(Et)—.

When [B] represents a —Ph— bivalent radical, the COR$_6$ group can be in ortho, meta or para position. It is preferably found in the para position.

When (D)$_{0-6}$ is a bivalent radical derived from a saturated or unsaturated, linear or branched, acyclic hydrocarbon containing 0 to 6 carbon atoms, (D)$_{0-6}$ is chosen from the values of [A] mentioned above. By (D)$_0$ is meant the absence of this radical which once again has a single covalent bond. (D) will preferably be a single bond or a (CH$_2$)$_n$ group, n being an integer chosen from 1, 2 or 3.

When Ra, Rb and Rc represent a (CH$_2$)$_{0-3}$—Ar, (CH$_2$)$_{0-3}$-Het, (CH$_2$)$_{0-3}$-Alk group, (CH$_2$)$_{0-3}$ represents either a single bond in the case of (CH$_2$)$_0$, or the radical —CH$_2$—, —(CH$_2$)$_2$— or —(CH$_2$)$_3$—.

By the term (Ar) representing a carbocyclic aryl group containing 6 to 18 carbon atoms is meant a radical derived from an aromatic cyclic hydrocarbon such as the phenyl, naphthyl, phenanthrenyl radical or a radical derived from a condensed bicyclic or tricyclic hydrocarbon containing a benzene ring such as indanyl, indenyl, dihydronaphthyl, tetrahydronaphthyl or fluorenyl. The junction occurs at the level of the benzene ring. It is preferably the phenyl.

By the term (Het) representing a radical derived from a saturated or unsaturated, aromatic or non-aromatic heterocycle containing 1 to 9 carbon atoms and 1 to 5 heteroatoms chosen from oxygen, nitrogen and sulphur atoms, is meant in particular:

monocyclic heterocyclic radicals, for example the following radicals: thienyl, furyl, pyrannyl, pyrrolyl, imidazolyl, pyrazolyl, pyridyl, pyrazinyl, pyrimidinyl, pyridazinyl, thiazolyl, oxazolyl, furazannyl, pyrrolinyl, imidazolinyl, pyrazolinyl, thiazolinyl, triazolyl, tetrazolyl, condensed heterocyclic rings, for example benzofurannyl, benzothienyl, benzimidazolyl, benzothiazolyl, naphtho[2,3-b]thienyl, thianthrenyl, isobenzofurannyl, chromenyl, xanthenyl, phenoxathiinyl, indolizinyl, isoindolyl, 3H-indolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, beta-carbolinyl, acridinyl, phenazinyl, phenothiazinyl, phenoxazinyl, indolinyl, isoindolinyl, imidazopyridyl, imidazopyrimidinyl or also the condensed polycyclic systems constituted by monocyclic heterocyclic radicals as defined such as for example furo[2,3-b]pyrrole or thieno[2,3-b]furan, or saturated heterocyclic radicals such as pyrrolidine, piperidine, morpholine.

This term (Het) includes furthermore the values of (Het') as defined previously.

By the term (Alk) representing a radical derived from a saturated or unsaturated, linear, branched or cyclic, non-aromatic hydrocarbon, is meant in the case of acyclic hydrocarbons the alkyl radicals such as methyl, ethyl, propyl, isopropyl, butyl, isobutyl, tert-butyl, n-pentyl, n-hexyl, 2-methyl pentyl, 2,3-dimethyl butyl, n-heptyl, 2-methylhexyl, 2,2-dimethylpentyl, 3,3-dimethyl pentyl, 3-ethylpentyl, n-octyl, 2,2-dimethylhexyl, 3,3-dimethylhexyl, 3-methyl-3-ethylpentyl, nonyl, 2,4-dimethylheptyl or n-decyl, the alkenyl radicals such as vinyl, propenyl, isopropenyl, allyl, 2-methylallyl, butenyl or isobutenyl, or the alkynyl radicals such as ethynyl, propynyl, propargyl, butynyl or isobutynyl, and in the case of the cyclic radicals, the cycloalkyl radicals, such as cyclopropyl, cyclobutyl, cyclopentyl, cyclohexyl or adamantyl.

When Ra and Rb represent together with the nitrogen atom to which they are linked a nitrogenous heterocycle, they are in particular the following saturated heterocycles: morpholine, piperidine, piperazine, pyrrolidine, or the unsaturated heterocycles such as pyrimidine, pyridine or pyrazine.

When R$_2$, R$_3$, R$_4$ and R$_5$ represent an O-(Alk) radical containing 1 to 12 carbon atoms, they are preferably methoxy, ethoxy, propyloxy, isopropyloxy, butyloxy, allenyloxy or propargyloxy. When R$_2$, R$_3$, R$_4$ and R$_5$ represent an O—(CH$_2$)$_{0-3}$—Ar radical they are preferably the phenylethoxy and phenylpropyloxy radicals.

When R$_2$ and R$_3$ form together a ring of —O—(CRdRe)$_n$—O— type, n being an integer from 1 to 5, it is in particular the —O—CH$_2$—O, O—C(Me$_2$)—O, O—C(Ph$_2$)—O radicals. R$_2$ and R$_3$ must each be in ortho position.

When R$_6$ represents an O-Alk or O-Ar radical, Alk and Ar being substituted or non-substituted, it is in particular one of the following radicals: (C$_1$–C$_8$)alkoxy, (C$_1$–C$_{14}$)aryl, (C$_1$–C$_8$)alkoxy, (C$_6$–C$_{14}$)aryloxy, (C$_1$–C$_8$)alkylcarboxyloxy, (C$_1$–C$_8$)dialkylaminocarbonylmethoxy, (C$_6$–C$_{14}$)aryl, (C$_1$–C$_8$)dialkyl-aminocarbonylmethoxy.

When R$_6$ represents an NH-alk, NH(alk)$_2$ or NH—Ar radical, it is in particular one of the following radicals: (C$_1$–C$_8$)alkylamino, di-(C$_1$–C$_8$)alkylamino, (C$_6$–C$_{14}$)aryl, (C$_2$–C$_8$)alkylamino, (C$_6$–C$_{14}$)arylamino.

When R$_6$ represents the remainder of an amino acid it can be an L or D amino acid.

The L or D amino acids can be natural or non-natural. They are preferably α-amino acids. For example, those described in Houben-Weyl, Methoden der organischen Chemie, Volume XV/1 and 2, Georg Thieme Verlag, Stuttgart, 1974: Aad, Abu, γAbu, Abz, 2Abz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hIle, hLeu, hLys, hMet, hphe, hpro, hSer, hThr, hTrp, hTyr, Hyl, Hyp, 3Hyp, Ile, Ise, Iva, Kyn, Lant, Lcn, Leu, Lsg, Lys, βLys, Δlys, Met, Mim, Min, nArg, Nle, Nva, Oly, Orn, Pan, Pec, Pen, Phe, Phg, Pic, Pro, Δpro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val, tert-butylglycine (Tbg), Neopentylglycine (Npg), Cyclohexylglycine (Chg), Cyclohexylalanine (Cha), 2-Thienylalanine (Thia), 2,2-diphenylaminoacetic acid, 2-(p-tolyl) 2-phenylamino acetic acid, 2-(p-chlorophenyl) amino acetic acid, or also 2-pyrrolidine acetic acid, 1,2,3,4-tetrahydroisoquinoline 3-acetic acid, decahydroisoquinoline 3-acetic acid, octahydroisoindol 2-acetic acid, decahydroquinoline 2-acetic acid, octahydrocyclopenta[b}pyrrol 2-carboxylic acid, 2-azabicyclo[2,2,2]octan-3-carboxylic acid, 2-azabicyclo[2,2,1]heptan-3-carboxylic acid, 2-azabicyclo[3,1,0]hexan-3-carboxylic acid, 2-azaspiro[4,4] nonan-3-carboxylic acid, 2-azaspiro[4,5]decan-3-carboxylic acid, spiro (bicyclo[2,2,1]heptan)-2,3-pyrrolidin-5-carboxylic acid, spiro (bicyclo[2,2,2]octan)-2,3-pyrrolidin-5-carboxylic acid, 2-azatricyclo[4,3,0,1$^{6,9}$]decan-3-carboxylic acid, decahydrocyclohepta[b]pyrrol-2-carboxylic acid, decahydrocycloocta[c]pyrrol-2-carboxylic acid, octahydrocyclopenta[c]pyrrol-2-carboxylic acid, octahydroisoindol-1-carboxylic acid, 2,3,3a,4,6a-hexahydrocyclopenta[b]pyrrol-2-carboxylic acid, 2,3,3a,4,5,7a-hexahydroindol-2-carboxylic acid, tetrahydrothiazol-4-carboxylic acid, isoxazolidin-3-carboxylic acid, pyrazolidin-3-carboxylic acid, hydroxypyrrolidin-2-carboxylic acid, which if appropriate, can be substituted (see the following formulae):

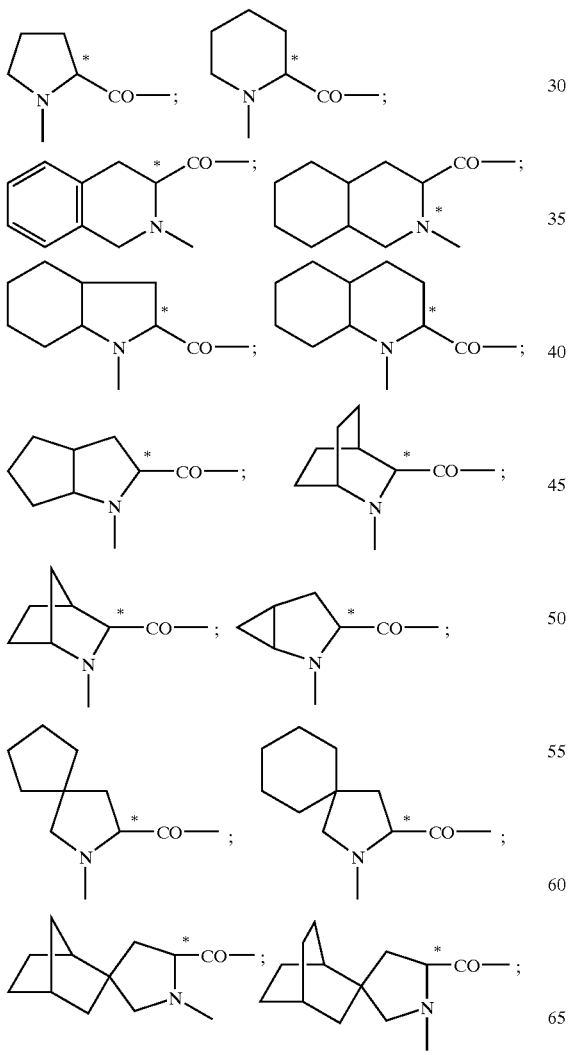

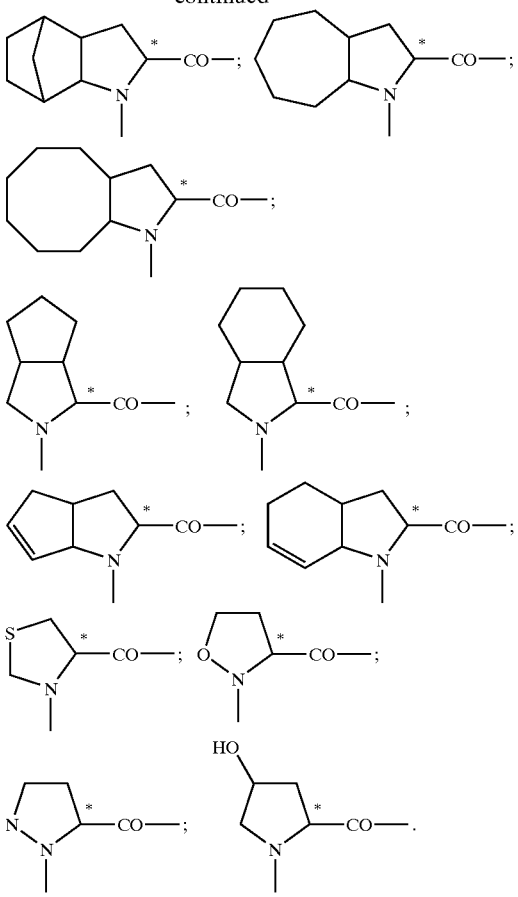

The heterocyclic remainders as described above are known for example from the following Patents or Patent Applications:

U.S. Pat. No. 4,344,949; U.S. Pat. No. 4,374,847; U.S. Pat. No. 4,350,704; EP-A-29,488; EP-A-31,741; EP-A-46,953; EP-A-49,605; EP-A-49,658; EP-A-50,800; EP-A-51,020; EP-A-52,870; EP-A-79,022; EP-A-84,164; EP-A-89,637; EP-A-90,341; EP-A-90,362; EP-A-105,102; EP-A-109,020; EP-A-111,873; EP-A-271,865 and EP-A-344,682.

In addition the amino acid can be in ester or amide form, such as for example, methyl ester, ethyl ester, isopropyl ester, isobutyl ester, tert-butyl ester, benzyl ester, ethylamide, semicarbazide or ω-amino ($C_2$–$C_8$)-alkylamide.

Finally, the functional groups of these amino acids can be protected. Suitable protective groups such as urethane protective groups, carboxyl protective groups or side-chain protective groups are described by Hubbuch, Kontakte (Merck) 1979, No 3, p. 14–23 and by Büllesbach, Kontakte (Merck) 1980, No 1, p. 23–35.

For example, the following can be mentioned: Aloc, Pyoc, Fmoc, Tcboc, Z, Boc, Ddz, Bpoc, Adoc, Msc, Moc, Z($NO_2$), Z($Hal_n$), Bobz, Iboc, Adpoc, Mboc, Acm, tertbutyl, Obzl, Onbzl, Ombzl, Bzl, Mob, Pic, Trt.

When G is a radical of formula G1

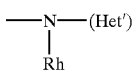

and (Het') is a heterocycle of general formula:

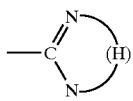

in which (H) forms, with the N=C—NH— unit, a saturated or unsaturated, mono- or bicyclic, aromatic or non-aromatic heterocycle containing 1 to 9 carbon atoms and 2 to 5 heteroatoms chosen from oxygen, nitrogen and sulphur atoms, this radical being able to be substituted or non-substituted, G1 represents in particular the following heterocycles:

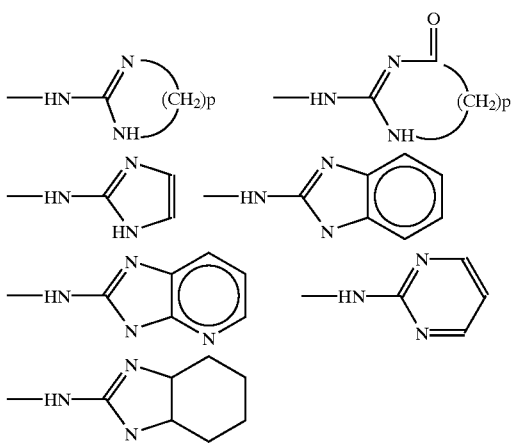

in which p represents an integer from 1 to 4.

When G is an —NRaRb radical (called G2), Ra and Rb can be a hydrogen atom, a $(CH_2)_{0-3}$—Ar, $(CH_2)_{0-3}$-Het or $(CH_2)_{0-3}$-Alk radical. The Ar, Het and Alk groups also being able to be substituted by groups as defined below.
G2 can be in particular an $NH_2$, NH-Alk group such as NHMe, NHeT, $N(Alk)_2$ group such as $NMe_2$, $NEt_2$, NMeEt, NH—$(CH_2)_{0-1}$—Ar group such as NHPh, $NHCH_2Ph$ or $NHCH_2$Het group such as $NHCH_2$-pyrrol-2-yl.

When Ra is a hydrogen atom or an (Alk) group and when Rb is a (Het') group the values of G1 are found.

When Ra and Rb form together with the nitrogen atom to which they are linked a nitrogenous heterocycle, it is in particular the heterocyclic groups as described above, these being able to be substituted or non-substituted.

When G is a (Het) radical (radical G3) this radical being able to be substituted or non-substituted, it is in particular the heterocycles listed above and especially the heterocycles of general formula (Het') as defined above. When this heterocycle is connected at the level of its nitrogen atom, the values of G2 are found in which Ra and Rb form a heterocycle with the nitrogen atom that carries them.

When G is an —NRh—C(=X)—NHRc radical (radical G4), or an $NRhSO_2Rc$ radical (radical G5), in which X is a sulphur or oxygen atom or NH, Rh and Rc are as defined previously, it is in particular one of the following groups:
—NH—C(=NH)—$NH_2$, —NH—C(=O)—$NH_2$ or —NH—C(=S)—$NH_2$, —NH—C(=NH)—$NHCH_2$—Ar such as —NH—C(=NH)—$NHCH_2$Ph, —NH—C(=NH)—$NHCH_2$-Het, —NH—C(=NH)—$NHCH_2$-Het', —NH—C(=NH)—NH-Alk such as —NH—C(=NH)—$NHCH_3$, or —NH—$SO_2$Ph, the Ar, Het, Het' or Alk groups being substituted or non-substituted.

The possible substituents of the (Alk), (Ar), (Het), (Het') or NRaRb radicals forming a heterocycle, are preferably the following radicals:

halogen: fluorine, chlorine, bromine, iodine,
alkyl, alkenyl, alkynyl containing 1 to 12 carbon atoms such as methyl, ethyl, propyl, isopropyl, butyl, isobutyl, tert-butyl, vinyl or allenyl; these radicals themselves being optionally substituted by one or more halogen atoms, for example fluorine such as trifluoromethyl,
oxo, cyano, nitro, formyl, carboxy and carboxyalkyl containing 1 to 6 carbon atoms, carboxamide,
alkoxy containing 1 to 12 carbon atoms such as methoxy, ethoxy, propyloxy, isopropyloxy, butyloxy,
alkylthio containing 1 to 12 carbon atoms such as methylthio, ethylthio, propylthio, isopropylthio, butylthio,
amino, alkylamino containing 1 to 12 carbon atoms such as methylamino or ethylamino, dialkylamino containing 2 to 24 carbon atoms such as dimethylamino, diethylamino, methylethylamino, each of these dialkylamino radicals optionally being in oxidized form,
aminoalkyl containing 1 to 12 carbon atoms such as aminomethyl or aminoethyl,
dialkylaminoalkyl containing 3 to 25 carbon atoms such as dimethylamino methyl or ethyl,
dialkylaminoalkyloxy containing 3 to 25 carbon atoms such as dimethylaminoethyloxy,
optionally acylated hydroxyl containing 1 to 12 carbon atoms, for example acetoxy,
acyl containing 1 to 12 carbon atoms such as formyl, acetyl, propionyl, butyryl, isobutyryl, valeryl, isovaleryl, succinyl, pivaloyl, benzoyl optionally substituted for example by a chlorine, iodine or fluorine atom; the chloroacetyl, dichloroacetyl, trichloroacetyl, bromoacetyl or trifluoroacetyl radicals can be mentioned,
carbocyclic or heterocyclic aryl such as phenyl, furyl, thienyl, pyridinyl or aralkyl such as benzyl, these radicals themselves being optionally substituted by halogen, alkyl, alkoxy, alkylthio, amino alkyl or dialkylamino indicated above.

Of course, one or more identical or different substituents can be present. In the case of (Het) the substituents can be at the level of the NH group or the carbon atom.

These substituents also illustrate the definition of $R_4$.

It is understood that when $R_1$, $R_2$, $R_3$, $R_4$, $R_5$, $R_6$, $R_a$, $R_b$, $R_c$ contain an alkyl, aryl or heterocyclic group as defined above, they can be identical or different independently of each other.

The invention naturally extends to the salts of the compounds of formula (I), such as for example the salts formed when the compounds of formula (I) contain an amino or amino guanidine function, with the following acids: hydrochloric, hydrobromic, nitric, sulphuric, phosphoric, acetic, trifluoroacetic, formic, propionic, benzoic, maleic, fumaric, succinic, tartaric, citric, oxalic, glyoxylic, aspartic, alkanesulphonic such as methane- or ethanesulphonic, arenesulphonic, such as benzene or paratoluene sulphonic and arylcarboxylic, or when the compounds of formula (I) contain an acid function, with alkali metal or alkaline-earth salts or optionally substituted ammonium salts.

The invention also extends to the esters of the compounds of formula (I).

In a first preferred group, a subject of the invention is the compounds of general formula (I) as defined previously, corresponding to general formula (I'):

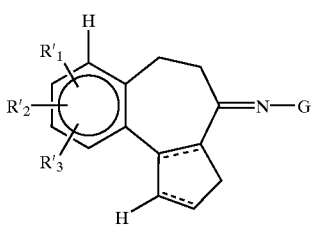

(I')

in which R'$_1$ represents one of the following groups:
—C≡C—[A']—[B']—COR'$_6$, —CH=CH—[A']—[B']—COR'$_6$, —(CH$_2$)$_2$—[A']—[B']—COR'$_6$, —O—[A']—[B']—COR'$_6$, —CH$_2$CO—[A']—[B]—COR'$_6$,
—[A']— representing a bivalent alkylene, alkenylene or alkynylene radical containing 1 to 6 carbon atoms,
[B'] representing a CH(Z') radical or a single bond,
Z' represents a hydrogen atom, one of the following groups: (CH$_2$)$_{0-6}$—NRaRb, (CH$_2$)$_{0-6}$—NH—SO$_2$—Rc, (CH$_2$)$_{0-6}$—NH—CO$_2$—Rc, (CH$_2$)$_{0-6}$—NH—CO—Rc, (CH$_2$)$_{0-6}$—NH—SO$_2$—NH—Rc, (CH$_2$)$_{0-6}$—NH—CO—NH—Rc, (CH$_2$)$_{0-6}$—CO$_2$—Rc, (CH$_2$)$_{0-6}$—SO$_2$—Rc, (CH$_2$)$_{0-6}$—CO—Rc or (CH$_2$)$_{0-6}$—Rc, Ra, Rb and Rc being as defined previously, R'$_6$ represents an OH, amino or alkoxy radical containing 1 to 8 carbon atoms, optionally substituted by one or more radicals chosen from hydroxy, amino, phenyl, alkylamino or dialkylamino radicals,
R'$_2$ and R'$_3$ represent a hydrogen atom or a methoxy radical, and G is as defined previously, the dotted lines represent an optional second bond, as well as the addition salts with acids and bases and esters.

In a second preferred group a subject of the invention is the compounds of general formula (I) as defined previously in which R$_6$ represents one of the following groups: —OH, —OCH$_3$, —OCH$_2$CH$_3$, —O—(CH$_2$)$_2$—OH,

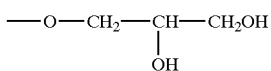

—O—(CH$_2$)$_2$—NH$_2$, —O—(CH$_2$)$_2$—N—(CH$_3$)$_2$, —NH$_2$ or —O—(CH$_2$)-phenyl, as well as the addition salts with acids and bases and esters.

In a third preferred group a subject of the invention is the compounds of general formula (I) as defined previously in which R$_1$ represents an O—(CH$_2$)$_{0-6}$CH(Z')—COOH or —(CH$_2$)$_{0-7}$—CH(Z')—COOH group, as well as the addition salts with acids and bases and the esters.

In a fourth preferred group a subject of the invention is the compounds of general formula (I) as defined previously, in which (Z') is a hydrogen atom, as well as the addition salts with acids and bases and the esters.

In a fifth preferred variant a subject of the invention is the compounds of general formula (I) as defined previously, in which (Z') is the (CH$_2$)$_{0-6}$—NH—CO$_2$—Rc or (CH$_2$)$_{0-6}$—NHRb group, Rb and Rc being as defined previously, as well as the addition salts with acids and bases and the esters.

In a sixth preferred group a subject of the invention is the compounds of general formula (I) as defined previously, in which Rb and Rc represent the (CH$_2$)$_{0-3}$—Ar group, Ar being as defined previously and being able to be substituted or non-substituted, as well as the addition salts with acids and bases and the esters.

In a seventh preferred group a subject of the invention is the compounds of general formula (I) as defined previously, in which G is a G4 group of formula —NH—C(=NH)—NHRc, Rc being as defined previously, as well as the addition salts with acids and bases and the esters.

In a eighth preferred group a subject of the invention is the compounds of general formula (I) as defined previously, in which G is a G4 group of formula NH—C(=NH)—NH$_2$, as well as the addition salts with acids and bases and the esters.

In an ninth preferred group a subject of the invention is the compounds of general formula (I) as defined previously, in which G is an —NH-Het' group as defined previously and in particular

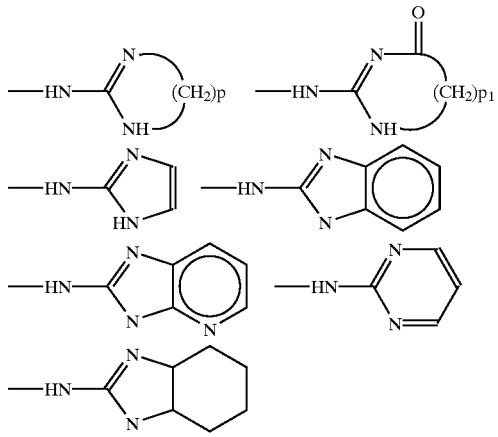

p being an integer equal to 2, 3 or 4, these heterocycles being substituted or non-substituted, as well as the addition salts with acids and bases and the esters.

In a tenth preferred group, a subject of the invention is the compounds of general formula (I) as defined previously, in which G is the group

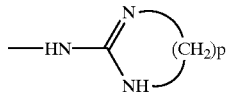

p being an integer equal to 2, 3 or 4, as well as the addition salts with acids and bases and the esters.

In an eleventh preferred group, a subject of the invention is the compounds of formula (I) as defined previously the names of which follow:
- 4-((4-((aminoiminomethyl)hydrazono)-9,10-dimethoxy-1,2,3,4,5,6-hexahydro-8-benz(e)azulen-yl)oxy)-butanoic acid,
- 5-((4-((aminoiminomethyl)hydrazono)-9,10-dimethoxy-1,2,3,4,5,6-hexahydro-8-benz(e)azulen-yl)oxy)-pentanoic acid,
- 5-((4-((aminoiminomethyl)hydrazono)-8,10-dimethoxy-1,2,3,4,5,6-hexahydro-9-benz(e)azulen-yl)oxy)-pentanoic acid,
- 6-((4-((aminoiminomethyl)hydrazono)-9,10-dimethoxy-1,2,3,4,5,6-hexahydro-8-benz(e)azulenyl)oxy)-hexanoic acid,
- 7-((4-((aminoiminomethyl)hydrazono)-9,10-dimethoxy-1,2,3,4,5,6-hexahydro-8-benz(e)azulenyl)oxy)-heptanoic acid,
- 5-((9,10-dimethoxy-1,2,3,4,5,6-hexahydro-4-((4,5-dihydro-1H-imidazol-2-yl)hydrazono)-8-benz(e)azulenyl)oxy)-pentanoic acid,
- ethyl 5-((4-((aminoiminomethyl)hydrazono)-9,10-dimethoxy-1,2,3,4,5,6-hexahydro-8-benz(e)azulenyl)oxy)-pentanoate hydrochloride, 4-((4-((aminoiminomethyl)hydrazono)-8,9-dimethoxy-1,2,3,4,5,6-hexahydro-10-benz(e)azulenyl)oxy)-butanoic acid, 5-((4-((aminoiminomethyl)hydrazono)-8,9-dimethoxy-1,2,3,4,5,6-hexahydro-10-benz(e)azulenyl)oxy)-pentanoic acid, 5-((4-(((amino)carbonyl)hydrazono)-9,10-dimethoxy-1,2,3,4,5,6-hexahydro-8-benz(e)azulenyl)oxy)-pentanoic acid, 5-((4-(((amino)thiocarbonyl)hydrazono)-9,10-dimethoxy-1,2,3,4,5,6-hexahydro-8-benz(e)azulenyl)oxy)-pentanoic acid, 4-((4-((aminoiminomethyl)hydrazono)-8,10-dimethoxy-1,2,3,4,5,6-hexahydro-9-benz(e)azulenyl)oxy)-butanoic acid, 6-((4-((4,5-dihydro-1H-imidazol-2-yl)hydrazono)-9,10-dimethoxy-1,2,3,4,5,6-hexahydro-8-benz(e)azulenyl)oxy)-hexanoic acid, 5-((4-((aminoiminomethyl)hydrazono)-9,10-dimethoxy-1,2,3,4,5,6-hexahydro-8-benz(e)azulenyl)oxy)-3,3-dimethyl-4-oxo-pentanoic acid, 5-((4-((4,5-dihydro-1H-imidazol-2-yl)hydrazono)-9,10-dimethoxy-1,2,3,4,5,6-hexahydro-8-benz(e)azulenyl)oxy)-3,3-dimethyl-4-oxo-pentanoic acid, 5-((4-((aminoiminomethyl)hydrazono)-9,10-dimethoxy-1,2,3,4,5,6-hexahydro-8-benz(e)azulenyl)oxy)-pentanoic acid hydrochloride, 4-((4-((4,5-dihydro-1H-imidazol-2-yl)hydrazono)-9,10-dimethoxy-1,2,3,4,5,6-hexahydro-8-benz(e)azulenyl)oxy)-butanoic acid, 5-((8-((aminoiminomethyl)hydrazono)-6,7,8,9,10,11-hexahydro-azuleno(5,6-d)-1,3-benzodioxol-4-yl)oxy)-pentanoic acid, 5-((8-((aminoiminomethyl)hydrazono)-2,2-diphenyl-6,7,8,9,10,11-hexahydro-azuleno(4,5-e)-(1,3)-benzodioxol-4-yl)oxy)-pentanoic acid, 4-((9,10-dimethoxy-4-((1,4,5,6-tetrahydro-2-pyrimidinyl) hydrazono)-1,2,3,4,5,6-hexahydro-8-benz(e)azulenyl)oxy)-butanoic acid, 2-((4-((4,5-dihydro-1H-imidazol-2-yl)hydrazono)-9,10-dimethoxy-1,2,3,4,5,6-hexahydro-8-benz(e)azulenyl)oxy)-ethanoic acid, 3-((4-((4,5-dihydro-1H-imidazol-2-yl)hydrazono)-9,10-dimethoxy-1,2,3,4,5,6-hexahydro-8-benz(e)azulenyl)oxy)-propanoic acid, 4-((4-((4,5-dihydro-1H-imidazol-2-yl)hydrazono)-1,2,3,4,5,6-hexahydro-8-benz(e)azulenyl)oxy)-butanoic acid, 4-((4-((4,5-dihydro-1H-imidazol-2-yl)hydrazono)-1,2,3,4,5,6-hexahydro-8-benz(e)azulenyl)oxy)-butanoic acid, O-[4[(4,5-dihydro-1H-imidazol-2-yl)hydrazono]-9,10-dimethoxy-1,2,3,4,5,6-hexahydro-8-benz[e]azulenyl]-N-[(phenylmethoxy)carbonyl]-DL-homoserine, O-[4[(4,5-dihydro-1H-imidazol-2-yl)hydrazono]-1,2,3,4,5,6-hexahydro-8-benz[e]azulenyl]-N-[(phenylmethoxy)carbonyl]-DL-homoserine, O-[4-[(1,2,3,4-tetrahydro6-pyrimidinyl)hydrazono]9,10-dimethoxy 1,2,3,4,5,6-hexahydro8-benz[e]azulenyl]N-[(phenylmethoxy)carbonyl]DL-homoserine, (2,3-dihydroxypropyl) ester of O-(9,10-dimethoxy 1,2,3,4,5,6-hexahydro4-[(1,4,5,6-tetrahydro2-pyrimidinyl) hydrazono]]-8-benz(e)azulenyl)N-[(phenylmethoxy)carbonyl]DL-homoserine, O-[4-[(4,5-dihydro1H-imidazol-2-yl)hydrazono]9,10-dimethoxy 1,2,3,4,5,6-hexahydro8-benz(e)azulenyl]N-[(8-quinolinyl)sulphonyl]DL-homoserine, monohydrochloride of O-[4-[(4,5-dihydro1H-imidazol-2-yl) hydrazono]9,10-dimethoxy1,2,3,4,5,6-hexahydro8-benz(e)-azulenyl]N-[[3-( 4-(3-pyridinyl)1H-imidazol-1-yl]propoxy]carbonyl]DL-homoserine, 5-[[4-[(4,5-dihydro4-oxo 1H-imidazol-2-yl)hydrazono]9,10-dimethoxy 1,2,3,4,5,6-hexahydro8-benz(e)azulenyl]oxy]pentanoic acid, O-[9,10-dimethoxy1,2,3,4,5,6-hexahydro4-[(4,5,6,7,-tetrahydro 1H-1,3-diazepin-2-yl)hydrazono]8-benz(e)-azulenyl]N-[(phenylmethoxy)carbonyl]DL-homoserine, O-[9,10-dimethoxy1,2,3,4,5,6-hexahydro4-[(3a,4,5,6,7,7a-hexahydro 1H-benzimidazol-2-yl)hydrazono]8-benz(e)azulenyl]N-[(phenylmethoxy)carbonyl]DL-homoserine.

Also a subject of the invention is a preparation process for the compounds of general formula (I) characterized in that a compound of formula (II):

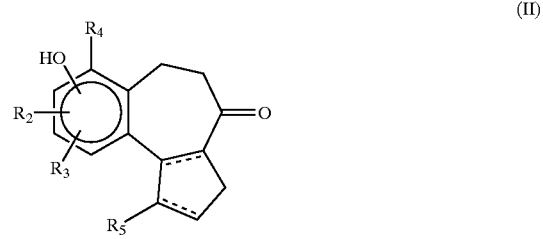

(II)

in which $R_2$, $R_3$, $R_4$ and $R_5$ are as described previously with the exception of the hydroxyl value, is subjected either to the action of a compound of formula (F1) in the presence of a base, Hal—[A]—[B]—COR$_6$     (F1)

or a compound of formula (F'$_1$) in the presence of a phosphine and of diethyl azodicarboxylate:

HO—[A]—[B]—COR$_6$     (F'$_1$)

in which Hal is a halogen atom, [A], [B] and $R_6$ are as described previously, [B] also being able to represent the

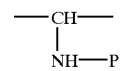

group, P being a protective group of the amine function, in order to obtain a compound of formula (IIIa):

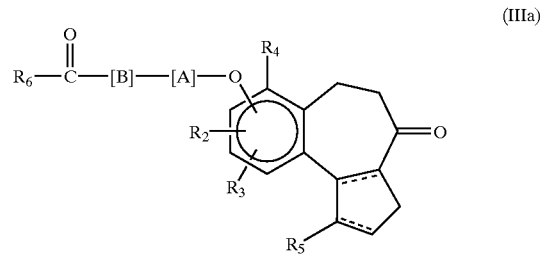

(IIIa)

or to the action of an activating group then of a compound of formula (F2) in the presence of a catalyst:

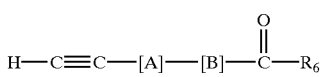
(F2)

in order to obtain a compound of formula (IIIb):

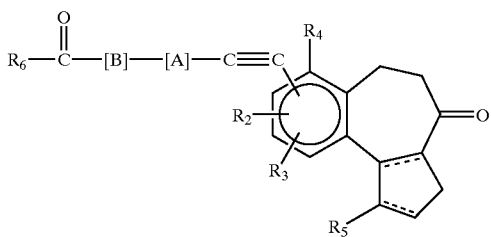
(IIIb)

which compounds of formula (IIIa) or (IIIb) are subjected to the action of a compound of formula (F3):

$H_2N-G$ (F3)

in which G is as described previously, in order to obtain the compounds of formula (IVa) and (IVb) corresponding to certain products of formula (I):

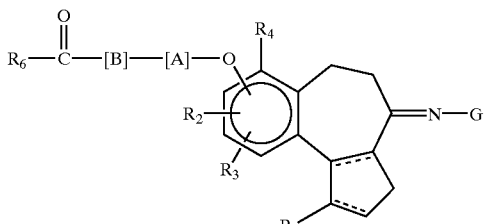
(IVa)

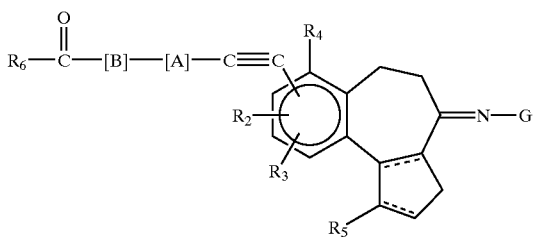
(IVb)

which are subjected, if appropriate, in a suitable order,

- to the action of a base or an acid in order to cleave the ester and to obtain the corresponding acid,
- to the action of a reducing agent suitable for partially or totally reducing the unsaturations of the $R_1$ group,
- to the action of a hydration agent of the triple bond,
- to the action of a dealkylation agent,
- to the action of a deprotection agent of the NH—P function in beta position of CO—$R_6$ when [B] represents the CH—NHP group,
- to the formation of the NH—$SO_2R_c$, NH—$CO_2R_c$, NHCOR$_c$, NH—$SO_2$—NH—$R_c$, NH—CO—NHR$_c$ group from the corresponding amine in beta position of COR$_6$, in order to obtain the corresponding compounds of formula (I) which are subjected if appropriate to the action of an acid or a base in order to obtain the corresponding salts or to the action of an esterification agent in order to obtain the corresponding esters.

The action of the compound of formula Hal-[A]—[B]—COR$_6$ (F1) is preferably carried out in the presence of a mineral base such as potassium carbonate or sodium carbonate in the presence of an aprotic dipolar solvent such as dimethylformamide. Hal is preferably a chlorine or bromine atom.

The action of the compound of formula HO—[A]—[B]—COR$_6$ (F'1) is carried out in the presence of a phosphine such as triphenylphosphine and of an agent such as diethyl azodicarboxylate (DEAD) in an aprotic solvent such as methylene chloride.

The action of the compound of formula H—C≡C—[A]—[B]—COR$_6$ (F2) is preceded by that of an activating group such as triflic anhydride of formula $(CF_3SO_2)_2O$ in the presence of a base such as pyridine in order to form the corresponding triflate of formula $(OSO_2CF_3)$ then carried out in the presence of a palladium derivative ($Pd^0$) such as $Pd(PPh_3)_4$.

The action of $NH_2$—G (F3) is carried out, either without solvent, or in an alcoholic solvent such as ethanol or butanol. The synthon $NH_2$—G is optionally used in the form of a salt such as the hydrochloride or the hydrobromide.

The saponification reaction of the ester function is carried out for example by the action of an alkaline base such as soda or potash in tetrahydrofuran or a lower alcohol such as methanol or ethanol. The ester can also be cleaved in an acid medium according to methods known by a man skilled in the art.

The reduction of the unsaturations can be carried out either totally by the action of hydrogen in the presence of a catalyst such palladium on charcoal or a rhodium catalyst such as Wilkinson's reagent or partially (alkynylene becomes alkenylene) by the action of a poisoned catalyst such as palladium on barium sulphate poisoned with pyridine or triethylamine.

The hydration reaction allowing a —$CH_2CO$—[A]—[B]—COR$_6$ group to be obtained from —C≡C—[A]—[B]—COR$_6$ is preferably carried out by the action of water in the presence of mercury sulphate.

The dealkylation reaction allowing the products of formula (I) with $R_2$, $R_3$, $R_4$ or $R_5$ representing hydroxyls to be obtained is carried out in the presence of aluminium chloride or boron tribromide.

The functionalization of $NH_2$ in alpha position of COR$_6$, [B] representing CH—$NH_2$ or CH—$NH_2$, HCl, is carried out according to standard methods known in organic chemistry.

The formation of NHSO$_2R_c$ from the corresponding amine is preferably carried out by the action of $R_cSO_2$Hal in the presence of a base for example triethylamine.

The formation of NHCO$_2R_c$ from the corresponding amine is preferably carried out by the action of $R_cOH$ according to the method described in J. Org. Chem., 61, 3929–3934 after having previously reacted the triphosgene in the presence of sodium bicarbonate in order to intermediately obtain the isocyanate.

The salification reactions can be carried out under the usual conditions. For example, in order to salify the terminal $CO_2H$ group of $R_1$, the operation is carried out in the presence of a sodium salt such as sodium carbonate or sodium or potassium acid carbonate.

Similarly, the salification of the amine or of the aminoguanidine which can be represented by G, by an acid, is carried out under the usual conditions. The operation is carried out for example with hydrochloric acid, for example in an ethereal solution.

The optional esterification of the products is carried out under standard conditions known to a man skilled in the art.

The operation is generally carried out by reacting the acid of formula (I) or a functional derivative with a reagent capable of introducing the ester group a non-exhaustive list of which is given above in the definition of $R_6$.

The products of general formulae (F1), (F'1), (F2), (F3) are known or prepared according to methods known to a man skilled in the art.

The grafting order of the different reagents can also be reversed, namely the compound of formula (II) is subjected to the action of a compound of formula F3 in order to intermediately obtain the product of formula (IIIc):

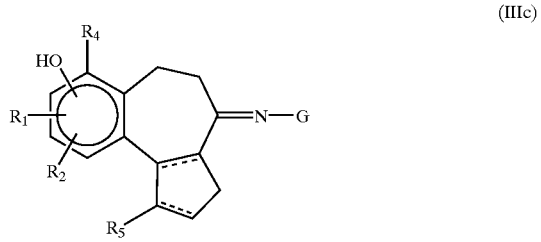

(IIIc)

which is subjected to the action of a compound of formula (F1), (F'1) or (F2) in order to obtain the corresponding products of formulae (IVa) and (IVb).

In this case, it may be necessary to provide protection of the G group of the product of formula (IIIc) then, after introduction of (F1), (F'1) or (F2), deprotection according to the methods known to a man skilled in the art (T. W. GREENE Protective Groups in Organic Synthesis. John Wiley and Sons Inc. 1991).

The deprotection reaction of the NH—P group in beta position of CO—$R_6$, [B] representing the CH—NHP group, is also carried out according to methods known to a man skilled in the art, in particular when P represents the $CO_2tBu$ group, by a decarboxylation reaction such as for example by the action of hydrochloric acid.

Bone is constantly subjected to a dynamic process which includes bone resorption and bone formation. These processes are mediated via specialized cells. Bone formation is the result of the deposit of a mineral matrix by osteoblasts and bone resorption is the result of the dissolution of this bone matrix by osteoclasts. Osteoporosis is characterized by a dry loss of this bone matrix. An activated mature osteoclast resorbs bone after adherence to the bone matrix by the secretion of proteolytic enzymes, and protons inside the adherence zone, resulting in depressions or holes in the surface of the bone which appear at the moment when the osteoclast detaches itself from the bone.

The compounds of formula (I) as well as their pharmaceutically acceptable addition salts have useful pharmacological properties. These compounds inhibit bone resorption which is mediated via the osteoclasts.

The compounds of the invention are therefore useful in the treatment of illnesses caused by loss of bone matrix, in particular osteoporosis, malignant hypercalcemia, osteopenia due to bone metastases, periodontitis, hyperparathyroidism, periarticular erosions in rhumatoid arthritis, Paget's disease, osteopenia induced by immobilization, glucocorticoid treatments or deficiencies in male or female sex hormones.

They can also be used for the treatment of inflammatory, cancerous and cardiovascular disorders including atherosclerosis, recurrence of stenosis.

They can finally be used as angiogenesis inhibitors and therefore in the treatment of tumours, by inhibition of their neovascularization, diabetic retinopathies and nephropathies.

Recent studies have shown that the fixing of the osteoclast to the bone is mediated by receptors: the integrins.

The integrins are a superfamily of receptors mediating the cell/cell and more particularly cell/matrix adherence processes, including in particular $\alpha 2b\beta 3$ as a blood platelet receptor (fibrinogen) and $\alpha v\beta 3$ as a receptor of vitronectin, and of bone sialoproteins such as osteopontin and thrombospondin.

These receptors which are protein heterodimers composed of two sub units $\alpha$ and $\beta$, possess fixation sites for divalent ions such as $Ca^{2+}$ in particular and a recognition site for their ligand predefined by the quality of their sub units.

The $\alpha v\beta 3$ receptor is a transmembrane glycoprotein which is expressed in a large number of cells including endothelial cells, smooth muscle cells, osteoclasts and cancerous cells which therefore bings about a pluripotentiality of the compounds according to the invention.

The $\alpha v\beta 3$ receptors expressed on the membrane of osteoclasts are the basis of the adherence/resorption process, contribute to the organization of the cellular cytoskeleton, and are implicated in osteoporosis (Ross et al., J. Biol. Chem., 1987, 262, 7703).

The $\alpha v\beta 3$ receptors expressed in the cells of the smooth muscle of the aorta stimulate their migration towards the neointima, which brings about the formation of atherosclerosis and the post-angioplastic reccurrence of stenosis (Brown et al, cardiovascular Res. (1994), 28, 1815).

The endothelial cells secrete growth factors which are mitogenic for the endothelium and can contribute to the formation of new blood vessels (angiogenesis). Angiogenic stimulation causes the formation of new blood vessels. Antagonists of the integrin $\alpha v\beta 3$ can therefore bring about a regression in cancerous tumours by inducing apoptosis of the angiogenic blood vessels. (Brook et al. Cell (1994) 79, 1157).

The natural ligands of the integrin $\alpha v\beta 3$ all contain the RGD unit (Arg-Gly-Asp). The peptides containing this RGD unit as well as anti $\alpha v\beta 3$ antibodies are known for their ability to inhibit the resorption of dentine, to prevent the adherence of the osteoclasts on the mineralized matrices (Horton et al. Exp. Cell. Res. (1991), 195, 368).

The peptide echistatin isolated from snake venom also containing an RGD unit is described as an inhibitor of the adherence of osteoclasts to bone, and is therefore a powerful inhibitor of bone resorption in tissues cultured in vitro (Sato et al. J. Cell. Biol. (1990), 111, 1713) and in vivo in a rat (Fisher et al. Endocrinology (1993), 132, 1441).

The compounds of formula (I) as well as their pharmaceutically acceptable addition salts and their esters may possess in particular an affinity vis-à-vis the vitronectin receptor $\alpha v\beta 3$ or vis-à-vis other integrins having vitronectin as ligand ($\alpha v\beta 1$, $\alpha v\beta 5$, $\alpha 2b\beta 3$) by inhibiting binding to their natural ligand.

This property therefore makes the compounds of the invention useful for the prevention or the treatment of illnesses the underlying pathology of which is caused by the ligands or cells which interact with the vitronectin receptor.

These compounds can also possess an activity vis-à-vis other integrins which interact with their ligand via the RGD tripeptide sequence, conferring them with pharmacological properties which can be used to treat pathologies associated with these receptors.

This activity vis-à-vis integrins therefore makes the compounds of the invention of use in the treatment of many illnesses such as those mentioned above or in the review by Dermot Cox DN&P 8(4) May 1995, 197–205 the content of which is integrated into the present Application.

A subject of the invention is therefore the compounds of formula (I) as medicaments, as well as their pharmaceutically acceptable addition salts and their esters.

Among the medicaments of the invention, there can be mentioned in particular the compounds described in the experimental part.

Among these products, a more particular subject of the invention is, as medicaments, the compounds of formula (I) listed previously.

The dosage varies according to the illness to be treated and the administration route: it can vary for example from 1 mg to 1000 mg per day for an adult by oral route.

The invention extends to the pharmaceutical compositions containing as active ingredient at least one medicament as defined above.

The compounds of formula (I) are used by digestive, parenteral or local route, for example by percutaneous route. They can be prescribed in the form of plain or sugar-coated tablets, capsules, granules, suppositories, pessaries, injectable preparations, ointments, creams, gels, microbeads, nanobeads, implants, patches, which are prepared according to the usual methods.

The active ingredient or ingredients can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The products of formula (II), in which the hydroxy radical hydroxy is in position 10, $R_2$ in position 8 and $R_3$ in position 9, represent an O-(Alk) or O—$(CH_2)_{0-3}$-Ar group, $R_4$ and $R_5$ are hydrogen atoms, are prepared according to the method described in the European Patent Application No. 0729933 and in the experimental part hereafter (Preparation 2).

The two other position isomers can be prepared in the following manner:

A compound of formula (IIA):

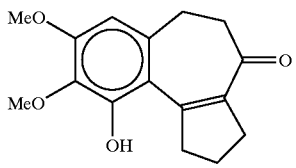

(IIA)

is subjected to the action of an alkylation reagent, in order to obtain the compound of formula (IIB):

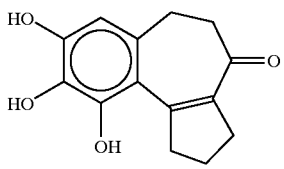

(IIB)

which compound of formula (IIB) is subjected: either to the action of a protection reagent of the diols in a basic medium, in order to selectively obtain the product of formula (IIC):

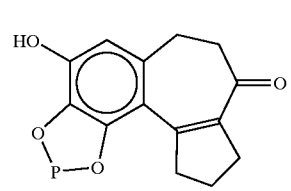

(IIC)

in which P represents the remainder of a protection reagent of the diols, which is successively subjected to the action of a protection reagent of the phenol, a deprotection reagent of the diols, an alkylation agent then a deprotection agent of the phenol in order to obtain the compound of formula (IID) corresponding to the trisubstituted product of formula (II) with OH in position 8:

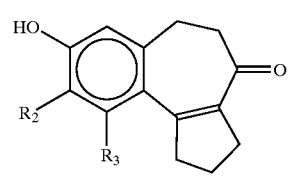

(IID)

or to the successive action of a protection agent of the phenol, an alkylation agent then a deprotection agent in order to obtain the compound of formula (IIE) corresponding to the trisubstituted product of formula (II) with OH in position 9:

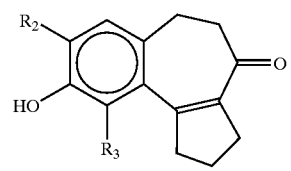

(IIE)

By dealkylation reagent is preferably meant agents such as boron tribromide or aluminium chloride.

The protection reagent of the diols which is reacted on the products of formula (IIB) can be a boron derivative such as boric acid, a trialkyl borate, for example a trimethyl or triethyl borate, or also borax.

By protection agent of the phenol is meant in particular a halide such as mesyl or tosyl chloride or bromide or also a benzylated derivative such as benzyl tosylate or mesylate.

By deprotection reagent of the diols is meant in particular a strong acid such as hydrochloric acid, sulphuric acid or paratoluene sulphonic acid or also an oxidizing agent, for example hydrogen peroxide, in the case of a protection by a boron derivative.

By alkylation agent is meant any standard agent known to a man skilled in the art for alkylating the phenols. There can be mentioned for example an alkyl halide such as methyl or ethyl chloride, an alkyl sulphate such as methyl or ethyl sulphate or also diazomethane.

By deprotection agent is meant a base such as soda, potash or also sodium or potassium carbonate.

The monosubstituted products of formula (II), in which $R_2$, $R_3$, $R_4$ and $R_5$ represent a hydrogen atom, are prepared according to an analogous method to that described in the European Patent Application No. 0729933:

(i) A compound of formula (a):

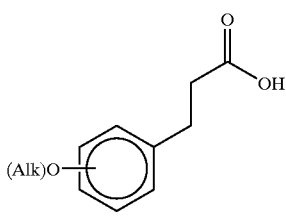

in which O-(Alk) is in meta or para position of the alkylcarboxylic group, (Alk) being as defined previously, is subjected to the action of a halogenation agent in order to obtain the corresponding acyl halide, (ii) Which is subjected to the action of a reagent of formula (b):

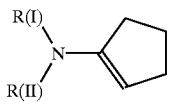

in which R(I) and R(II), identical or different, represent an alkyl group containing 1 to 6 carbon atoms, or R(I) and R(II) together with the nitrogen atom to which they are linked, represent a saturated or unsaturated heterocycle with 5 or 6 members optionally containing another heteroatom chosen from O and N, in Order to Obtain a Compound of Formula (c):

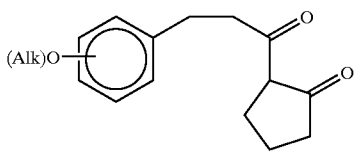

(iii) which is subjected to the action of a halogenation agent in order to obtain a compound of formula (d):

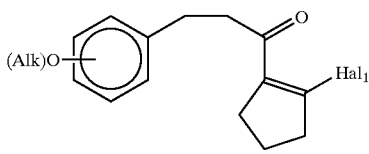

in which $Hal_1$ represents a halogen atom, (iv) which is subjected to the action of a Lewis acid, in order to obtain a compound of formula (e):

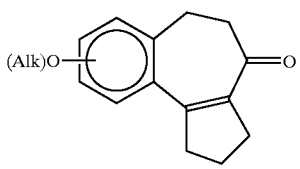

(v) which is subjected to a dealkylation reagent in order to obtain the product of formula (IIF) corresponding to the expected mronosubstituted product of formula (II):

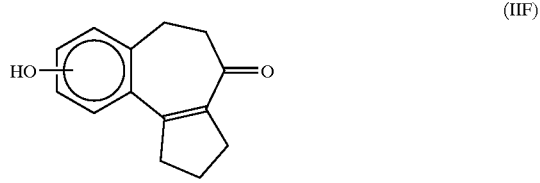

The disubstituted products of formula (II), in which $R_2$ represents O-(Alk) or O—$(CH_2)_{0-3}$—Ar, $R_3$, $R_4$ and $R_5$ are hydrogen atoms and OH and $R_2$ being in position 8, 9 or 10, are prepared according to the method as described above starting from the compound of formula (a'):

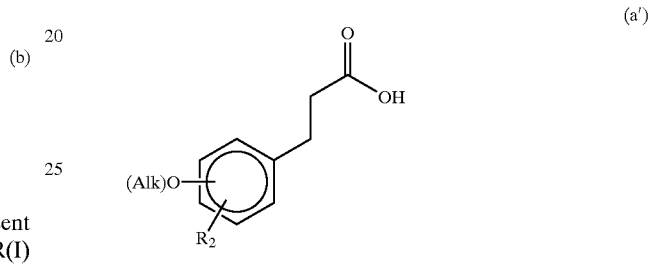

in which O-(Alk) and $R_2$ are in meta or para position of the alkyl carboxylic group, $R_2$ being an O-(Alk) or —$(CH_2)_{0-3}$—Ar group, which is successively subjected to reactions (i), (ii), (iii), (iv) and (v) and the products of formula (IIG) are obtained corresponding to the expected bisubstituted products of formula (II):

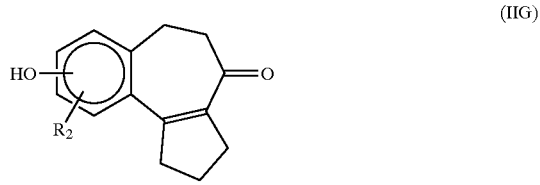

The halogenation agent which is reacted on the compound of formula (a) or (a') is for example thionyl chloride, oxalyl chloride or any other agent known to a man skilled in the art for preparing an acid halide.

The reagent of formula (b) is prepared starting from cyclopentanone and a secondary amine, for example diethylamine, piperidine, piperazine or, preferably, morpholine. The operation is carried out in the presence of a strong acid catalyst, for example paratoluene sulphonic acid.

The action of the enamine of formula (b) on the acid halide is preferably carried out in the presence of a tertiary amine such as triethylamine or pyridine.

The halogenation agent which is reacted on the compound of formula (c), or its disubstituted equivalent of formula (c'), can be for example thionyl chloride, phosgene, phosphorus oxychloride or, preferably, oxalyl chloride.

The Lewis acid used for cyclizing the compound of formula (d), or its disubstituted equivalent of formula (d') is for example aluminium chloride, titanium tetrachloride, or preferably ferric chloride, or tin tetrachloride. The reaction, like the preceding ones, can be carried out, for example, in a halogenated solvent such as methylene chloride, chloroform or dichloroethane.

The dealkylation reagent of the compound of formula (e), or its disubstituted equivalent of formula (e') in order to obtain the corresponding phenols is preferably aluminium chloride or boron tribromide.

The products of formula (II) in which $R_4$ is different from the hydrogen atom are prepared by standard methods of aromatic electrophilic and nucleophilic substitution known to a man skilled in the art.

The products of formula (II) in which $R_5$ is different from the hydrogen atom are prepared according to methods known to a man skilled in the art and in particular according to the method described in the European Patent Application No. 0729933, that is to say by halogenation then the action of water or a suitable alcohol.

The products of formula (II) in which $R_5$ is a hydrogen atom and in which there is a double bond in position 1–2 are prepared according to methods known to a man skilled in the art and in particular according to the method described in the European Patent Application No. 0729933, that is to say by dehydration or dealkoxylation in anhydrous acid medium.

The products of formula (II) in which the junction between the ring in position 5 and the ring in position 7 is saturated are prepared according to standard hydrogenation methods in particular in the presence of palladium on charcoal of the corresponding double bond.

The introduction of $R_4$, $R_5$ as well as the hydrogenation reaction is preferably carried out on the compounds of formula (IIA), (IID), (IIE), (IIF) or (IIG).

The products of formula (II) in which $R_2$ and $R_3$, each in ortho position, form a ring of —O—(CRdRe)$_n$—O type as defined previously, are also prepared according to methods known to a man skilled in the art and in particular according to the method described hereafter in the experimental part.

A subject of the invention is also, as intermediate products, the products of formulae (IIIa), (IIIb), (IIIc) and (II), it being understood that the compounds of formula (IIc) and the following compounds:

2,3,5,6-tetrahydro-9,10-dimethoxy-8-hydroxy-benz[e]azulen-4(1H)-one, and 2,3,5,6-tetrahydro-8,9-dimethoxy-10-hydroxy-benz[e]azulen-4(1H)-one, are excluded. The preparation of these 2 compounds appears hereafter in the experimental part.

The following examples illustrate the invention without however limiting it.

PREPARATION 1

2,3,5,6-Tetrahydro-8,9,10-trihydroxy-benz[e]-azulen-4(1H)-one

Stage A: 3,4,5-Trimethoxy-benzenepropanoic Acid 6.8 g of potassium carbonate is added to a solution of 21.44 g of 3,4,5-trimethoxyphenylpropenoic acid and 45 ml of water then the medium is hydrogenated for one hour under a pressure of 1200–1300 mbars in the presence of 1.8 g activated charcoal with 10% palladium, in this way 2.1 l of hydrogen is absorbed. The reaction medium is filtered, followed by washing with water and acidifying with 50 ml of hydrochloric acid (2N). After separation, the residue is washed with water and dried under reduced pressure at ambient temperature. In this way 19.8 g of the expected product is obtained (M.P.=102–103° C.)

IR Spectrum (CHCl$_3$); Carbonyl: {1712 cm$^{-1}$ (max) aromatic: {1592 cm$^{-1}$; {1740 cm$^{-1}$ (sh) {1510 cm$^{-1}$; NMR Spectrum (CDCl$_3$); 2.69 t)} =C—CH$_2$—CH$_2$—CO 3.83 (s)} 3 H$_3$CO—C—; 2.91(t)} | 3.85(s)}; 6.43(s) aromatic 2H's; 10.50 (m) mobile 1H.

Stage B: 3,4,5-Trimethoxy-benzenepropanoyl Chloride

A solution of 6 g of the product obtained in Stage A in 21 ml of methylene chloride is dried with 1.5 g of magnesium sulphate, after filtration the reaction medium is cooled down to 5° C. and 2.2 ml of thionyl chloride is added then the solution is agitated for 20 hours at ambient temperature. It is evaporated to dryness under reduced pressure by proceeding with two entrainments with cyclohexane and in this way 6.46 g of the sought product is collected. (M.P.=60° C.)

Stage C: 2-[3-(3,4,5-Trimethoxyphenyl)-1-oxopropyl]-cyclopentanone

A solution of 4.27 g of the product obtained in Stage B in 15 ml of methylene chloride is added over one hour 30 minutes at +5° C. to a solution, cooled down to 5° C., of 2.4 ml of 1-(N-morpholinyl)cyclopentene obtained as described hereafter, 2.31 ml of triethylamine and 15 ml of methylene chloride. The reaction medium is agitated for one hour at +5° C. then while allowing the temperature to rise 10 ml of 2N hydrochloric acid is added, followed by agitation for hour at ambient temperature, decanting, washing with water then with a saturated solution of sodium bicarbonate, drying, filtering and evaporating to dryness under reduced pressure. 5 g of the expected product is obtained. The crude product is purified by dissolution in 10 volumes of ethyl acetate, extracted with an N soda solution, the alkaline phase is washed with ethyl acetate, acidification is carried out to pH 1 with concentrated hydrochloric acid, followed by extraction with methylene chloride, drying and evaporating to dryness under reduced pressure. 2.75 g of purified product is collected.

IR Spectrum (CHCl$_3$): Carbonyl: {1741 cm$^{-1}$ aromatic: {1592 cm$^{-1}$; {1709 cm$^{-1}$ {1509 cm$^{-1}$; Carbonyl: {1658 cm$^{-1}$; +C=C {~1610 cm$^{-1}$ with OH in chelated form NMR Spectrum (CDCl$_3$); 6.41(s) arom. 2H (integration base); 3.81(s) 3.82(s)} 9H in all; 3.83(s) 3.85(s)} 4 types of

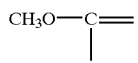

1.86(m) CH$_2$—CH$_2$—CH$_2$ ~1.5H; 1.95 to 2.95(m) ~7.5H in all of which =C—CH$_2$ of several types; 3.26(t) ~0.4H

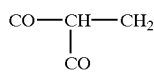

11.2 (wide m) mobile H.

Preparation of 1-(N-Moroholinyl)-cyclopentene Used in Stage C

A solution of 100 ml of cyclohexane, 20 ml of cyclopentanone, 50 ml of morpholine and 100 mg of para-toluene sulphonic acid is agitated for 4 hours 30 minutes under reflux, eliminating the water formed. After evaporation of the solvent under reduced pressure, distillation is carried out under 12–13 mbars of pressure and 27.44 g of sought product is collected (B.p.=83° C.).

Stage D: 1-(2-Chloro-1-cyclopenten-1-yl)-3-(3,4,5-trimethoxyphenyl)-propan-1-one 13 ml of oxalyl chloride is added at ambient temperature to a solution of 23 g of product obtained in Stage C and 230 ml of chloroform. The reaction medium is agitated for three hours at ambient temperature, and concentrated under reduced pressure by proceeding with two entrainments with cyclohexane. 28 g of crude product is obtained which is recrystallized from a mixture of 50 ml of cyclohexane and 50 ml of diisopropyl ether after partial concentration. The crystals are separated out, washed with diisopropyl ether and dried under pressure. 16.24 g of the expected product is obtained. (M.P.=93° C.).

IR Spectrum (CHCl$_3$): 1659 cm$^{-1}$: Carbonyl; 1599 cm$^{-1}$; 1586 cm$^{-1}$: C=C+aromatic; 1508 cm$^{-1}$; NMR Spectrum CDCl$_3$; 1.93 (m): central CH$_2$; 2.69 (m)–2.81 (m): C—CH$_2$—C= of the cyclopentene; 2.85 (t,j=7.5)–3.08 (t,j=7.5): the other =C—CH$_2$—C's; 2.44: CH$_3$—C=; 3.68–3.81: the OCH$_3$s; 6.59–6.68(d,j=2): the meta coupled aromatic CH='s; 7.31–7.80(d,j=8): the aromatics.

Stage E: 2,3,5,6-Tetrahydro-8,9,10-trimethoxy-benz[e] azulen-4(1H)-one 900 mg of the product obtained in Stage D, 9 ml of 1,2-dichloroethane and 0.9 ml of stannic chloride are agitated for 20 hours at ambient temperature. 9 ml of water and ice is then added and the mixture is decanted, washed with water, reextraction is carried out once with methylene chloride, followed by drying over magnesium sulphate, filtration and evaporation to dryness under reduced pressure, to obtain 1 g the expected (crude) product which is purified by chromatography on silica, eluting with cyclohexane with 10% ethyl acetate, then with 25% ethyl acetate. After concentration, 700 mg of product is collected which is crystallized from 5 ml of n-hexane, followed by cooling down to 0° C., separation, washing with the minimum amount of n-hexane, and drying under reduced pressure at ambient temperature in order to obtain 630 mg of expected product. (M.P.=101–102° C.). NMR Spectrum (CDCl$_3$); 1.86 (m) the central CH$_2$; 2.65(dd) 2H} 3.84}; 2.72(t) 2H} the other CH$_2$'s 3.86} the OMe's; 2.84(dd) 2H} 3.90}; 3.06 2H}; 6.59(s) aromatic H.

Stage F: 2,3,5,6-Tetrahydro-8,9,10-trihydroxy-benz[e] azulen-4(1H)-one

By operating as in Stage B of Preparation 1a, the expected demethylated product is obtained.

PREPARATION 1a 2,3,5,6-Tetrahydro-8,9,10-trihydroxy-benz-[e] azulen-4(1H)-one

Stage A: 2,3,5,6-Tetrahydro-8,9,10-trimethoxy-benz[e] azulen-4(1H)-one 60 g of the product obtained in Preparation 2, 600 ml of 1,2-dichloroethane, 342 ml of 2N soda, 1.2 g of tetrabutylammonium bromide and 33 ml of dimethyl sulphate are agitated for 2 hours 30 minutes at 20° C. 39 ml of triethylamine is then introduced in order to destroy the excess dimethyl sulphate and agitation is carried out for one hour at 20° C.±2° C. 342 ml of demineralized water is added, followed by agitation for 15 minutes at 20° C.±2° C., and decanting, the aqueous phase is reextracted twice with 120 ml of 1,2-dichloroethane each time. The 1,2-dichloroethane phases are combined and washed with 4×240 ml of demineralized water, then with 1×300 ml of N hydrochloric acid, then with 3×240 ml of demineralized water (until neutrality is obtained). The combined organic phases are dried over sodium sulphate, filtered and concentrated under ordinary pressure at 83° C. to a residual volume of 480 ml.

Stage B: 2,3,5,6-Tetrahydro-8,9,10-trihydroxy-benz[e] azulen-4(1H)-one 480 ml of the solution obtained in (A) is heated under reflux for one hour with 102.3 g of anhydrous aluminium chloride. The medium is cooled down to 0° C.±2° C. then a mixture of 600 ml of demineralized water and 192 ml of pure sulphuric acid (concentrated) cooled down beforehand to about 0° C. is added over two hours while maintaining the temperature of the reaction medium below 20° C. 300 ml of demineralized water is introduced over 5 minutes at 20° C.±2° C. and agitation is carried out for 16 hours at 20° C.±2° C., followed by separation, washing twice with 60 ml of 1,2-dichloroethane each time, then with demineralized water, drying under reduced pressure, and 52.2 g of the sought product is obtained.

PREPARATION 2

8,9-Dimethoxy-10-hydroxy-2,3,5,6-tetrahydro-benz [e]azulen-4(1E)-one

Stage A: 3,4-Dimethoxy 5-[[(4-Methylphenyl)-sulphonyl]oxy]-benzenepropanoic Acid The operation is carried out as in Stage A of Preparation 1 using 29.76 g of 3,4-dimethoxy-5-[[[(4-methylphenyl)-sulphonyl]oxy]phenyl]-cinnamic acid the preparation of which is given hereafter, 43.5 g of potassium carbonate, 60 ml of methanol and 1.48 g of activated charcoal with 10% palladium. In this way 28.23 g of the sought product is obtained in the form of colourless crystals (M.P.=48–149° C.).

UV Spectrum (EtOH); For M=380.4; max 226 nm ε=22100; infl 263 nm ε=2000; infl 269 nm ε=2400; max 274 nm ε=2800; infl 279 nm ε=2500; infl 307 nm ε=450; NMR Spectrum (CDCl$_3$); 2.45(s) CH$_3$—; 2.61(m) =C—CH$_2$—CH$_2$—C= 3.68 (s) 2 CH$_3$O—C=; 2.86(m) 3.81(s); 6.61 (d,j=2) 7.32 (wd) H$_3$ H$_5$; 6.65(d,j=2) H$_4$ H$_6$ 7.80 (wd) H$_2$ H$_6$.

Stage B: 3,4-Dimethoxy 5-[[(4-Methylphenyl)-sulphonyl]oxy]-benzenepropanoyl Chloride The operation is carried out as in Stage B of Preparation 1 using 1.9 g of the product obtained in Stage A, 9.5 ml of methylene chloride and 0.7 ml of thionyl chloride. 2.24 g of the sought product is obtained, used as it is for the following stage.

Stage C: 2-[3-[3,4-Dimethoxy-5-[[(4-methylphenyl) sulphonyl)oxy]-phenyl]-1-oxopropyl]-cyclopentanone The operation is carried out as in Stage C of Preparation 1 starting with 2.24 g of the acid chloride obtained in Stage B and using 770 mg of 1-(N-morpholinyl)cyclopentene (prepared in Stage C of Preparation 1), 6 ml of methylene chloride and 0.77 ml of triethylamine. After recrystallization from diisopropyl ether, 1.27 g of the sought product is obtained (M.P.=84° C.).

IR Spectrum (CHCl$_3$); Carbonyl: {1742 cm$^{-1}$ O—SO$_2$ {1374 cm$^1$; {1709 cm$^{-1}$ 1178 cm$^{-1}$ 1658 cm$^{-1}$; C=C+ aromatic {1608 cm$^{-1}$ 1599 cm$^{-1}$ 1586 cm$^{-1}$ 1508 cm$^{-1}$; NMR Spectrum (CDCl$_3$); 2.44(s) CH$_3$—O; 3.67(s)} 2 OCH$_3$; 3.79(s) 3.81(s)}; 6.59 to 6.65 (m) arom. 2H in ortho position of the O's. 7.32(wd) H$_3$ H$_5$; 7.89(wd) H$_2$ H$_6$; 13.58(wide m) enol form OH; 1.8 to 3.4(m) 10 to 11 H other protons; UV Spectrum; 1-EtOH (+dioxane) for M 446.52; max 225 nm ε=23000; max 282 nm ε=7900; infl 270, 277, 290, 300, 313 nm; 2-EtOH (0.1N NaOH); max 310 nm ε=21600; infl 268, 272, 276 nm;

Stage D: 1-(2-Chloro-1-cyclopenten-1-yl)-3-[3,4-dimethoxy-5-[[(4-methylphenyl)sulphonyl]oxy]-phenyl]-propan-1-one The operation is carried out as in Stage D of Preparation 1 using 8.7 g of the product obtained in Stage C, 70 ml of chloroform and 3.5 ml of oxalyl chloride. After crystallization from diisopropyl ether, 7.75 g of the sought product is obtained (M.P.=73° C.). This product is used as it is for the following stage.

An analytical sample was obtained by recrystallization from 2.5 volumes of methylene chloride and 5 volumes of diisopropyl ether followed by concentration to 3 volumes, separation, washing with diisopropyl ether and drying under reduced pressure at ambient temperature (M.P.=77–78° C.).

IR Spectrum (CHCl₃); Carbonyl: {1659 cm⁻¹; Aromatic C=C: {1599 cm⁻¹–1586 cm⁻¹–1508 cm⁻¹; UV Spectrum (EtOH); max 227 nm ε=26100; infl 248 nm ε=12800; infl 272 nm ε=5300; infl 280 nm ε3200; infl 320 nm; NMR Spectrum (CDCl₃); 1.93(m) central —C—CH₂—C—}; 2.69(m)} the C—CH₂—C='s}; 2.81(m}}}; 2.85(t,j=7.5)} the other =C—CH₂—C's; 3.08(t,j=7.5)}; 2.44 CH₃—C=; 3.68} the OCH₃'s; 3.81}; 6.59(d,j=2) the aromatic CH's; 6.68(d,j=2) meta coupled; 7.31(d,j=8)}; 7.80(d,j=8)}.

Stage E: 8,9-Dimethoxy-10-[[(4-methylphenyl)sulphonyl] oxy]-2,3,5,6-tetrahydro-benz[e]azulen-4(1H)-one 1.65 g of 98% ferric chloride is added at ambient temperature to a solution of 2.32 g of the product obtained in Stage C in 50 ml of 1,2-dichloroethane. The mixture is agitated for 48 hours at ambient temperature then poured into a mixture of water and ice, vigorous agitation is carried out for 15 minutes followed by extraction with methylene chloride, the extracts are washed with water, then with a saturated aqueous solution of sodium chloride. After drying and evaporation to dryness under reduced pressure, 2.15 g of the crude product is obtained which is chromato-graphed, eluting with cyclohexane with 50% ethyl acetate, 1.8 g of product is collected which is chromatographed again and recrystallized from a chloroform/diisopropyl ether mixture in order to obtain 720 mg of the sought product (M.P.=138° C.). IR Spectrum (CHCl₃); Carbonyl: {1650 cm⁻¹; {1599 cm⁻¹; C=C+{1556 cm⁻¹; aromatic {1512 cm⁻¹–1498 cm⁻¹; UV Spectrum (EtOH); max 230 nm ε=25300; infl 254 nm ε=9400; max 323 nm ε=10300; NMR Spectrum (CDCl₃); ~1.61(m) (2H) central CH₂; ~2.41 Ph—CH₃; ~2.50 to 2.80

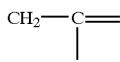

3.88(s)} the OCH₃'s; 3.90(s)}; 6.74 H4; 7.21(d)} C—Ph—SO₂; 7.64(d)}.

Stage F: 8,9-Dimethoxy-10-hydroxy-2,3,5,6-tetrahydro-benz[e]azulen-4(1H)-one

A mixture of 350 g of the product obtained in Stage E above, 1750 ml of methanol, 350 ml of demineralized water and 350 ml of pure caustic soda lye (concentrated) is heated under reflux for 2 hours. The reaction medium is cooled down to about 2° C.±2° C. and 467 ml of concentrated hydrochloric acid is introduced over 45 minutes while maintaining the temperature at 2° C.±2° C. 1645 ml of demineralized water is then added over 10 minutes while maintaining the temperature at 2° C.±, then the reaction medium is agitated for 30 minutes still at 2° C.±2° C. The crystals formed are separated out, washed by clarifications taking up 5 times each time with 700 ml of demineralized water at 20° C. then dried at 40° C. under reduced pressure in order to obtain 199.1 g of the sought product.

Preparation of 3,4-Dimethoxy 5-[(4-Methylphenyl)-sulphonyl]-oxy]-cinnamic Acid Used at the Start of Preparation 2

Stage A: Methyl 3,4-Dimethoxy-5-[[(4-methylphenyl)-sulphonyl]oxy]-benzoate.

303 ml of triethylamine is added over 10 minutes at ambient temperature to an agitated mixture of 200 g of methyl gallate and 2 liters of methylene chloride. After dissolution, the reaction medium is cooled down to 0–5° C. then 130 ml of dichlorodimethylsilane is added over one hour at this temperature, agitation is carried out for a further 30 minutes at this temperature. While maintaining the temperature at 0–5° C., 303.2 ml of triethylamine is added over 25 minutes then 227.6 g of tosyl chloride is added over 15 minutes. Agitation is continued for one hour at 0–5° C., and 200 ml of acetic acid then 500 ml of demineralized water are added over 10 minutes under agitation and while allowing the temperature to rise to 20–22° C., and agitation is continued for 15 minutes at 20° C. The methylene chloride is distilled off at a constant volume (3.3 l) under reduced pressure replacing it with demineralized water, agitation is carried out for 2 hours at 20° C., followed by separation, washing with demineralized water, in order to obtain 523 g (damp weight) of methyl 3,4-dihydroxy-5-[[(4-methylphenyl)-sulphonyl]oxy)benzoate (methyl 3-tosylgallate). The damp product obtained is taken up in 2.17 l de soda (2N) and 2.17 l of methylene chloride. Agitation is carried out at 20° C. until dissolution is achieved then 18 g of tetrabutylammonium bromide is added at 20° C. then, over 15 minutes at 20° C., 237 ml of dimethyl sulphate is added. The reaction medium is agitated for 1.5 hours at 20–22° C. 78 ml of triethylamine is added at 20–22° C. and agitation is carried out overnight at 20–22° C., followed by decanting and washing with 400 ml of demineralized water, 20 ml of pure acetic acid is added to the organic phase, followed by agitation for 15 minutes, adding 400 ml of demineralized water then decanting. The combined organic phases are concentrated to dryness, firstly under atmospheric pressure then under reduced pressure at 40 mm Hg and 60° C. outside temperature. Entrainment is carried out with 400 ml of methanol then the dry extract obtained is taken up in 600 ml of methanol, heated under reflux until the product has totally dissolved, followed by cooling down to 0–5° C. and agitation for one hour at this temperature. After separation, washing twice with 200 ml of methanol at –10° C. and drying at 40° C. under reduced pressure, 330.4 g of methyl 3,4-dimethoxy-5-[[(4-methylphenyl)-sulphonyl] oxy]-benzoate is thus collected. The crude product is purified by recrystallization from 330 ml of toluene. After 2 hours of agitation at –10° C., separation is carried out, followed by washing twice with 82 ml of toluene, cooling down to –15° C. and drying under reduced pressure at 40° C. in order to obtain 230.3 g of the purified sought product.

Stage B: 3,4-Dimethoxy 5-[[(4-Methylphenyl)sulphonyl] oxy]cinnamic Acid a) 600 ml of toluene is cooled down to 0° C. and 202 ml of a Vitride® solution at 70% in toluene is added at 0° C. and 67.6 ml of morpholine is added over one hour at 0–2° C., and the temperature is allowed to rise to 18° C. The solution thus obtained is used immediately for the following stage.

b) 200 g of methyl 3,4-dimethoxy-5-[[(4-methylphenyl) sulphonyl]oxy]-benzoate obtained in Stage A and 1400 ml of toluene are agitated for 10 minutes at 20–22° C. until total dissolution is obtained. The reagent solution obtained above is added over one hour at 10° C. Agitation is continued for one hour while allowing the temperature to rise to 18° C. A solution cooled down to 10° C. of 200 ml of concentrated sulphuric acid and 1000 ml of demineralized water is introduced over one hour at 10° C. Agitation is carried out for 16 hours at 20° C. then the organic phase is decanted, washed with 5×200 ml of demineralized water, dried, filtered and washed with 3×100 ml of methylene chloride. The intermediate aldehyde solution thus obtained is used as it is for the following stage.

c) The intermediate aldehyde solution obtained above, 200 ml of 2-picoline, 120 g of malonic acid and 20 ml of piperidine are heated for 16 hours at 70° C.±2° C. (while eliminating the methylene chloride under ordinary pressure).

The reaction medium is cooled down to 20–22° C., and while maintaining this temperature a solution of 200 ml of concentrated hydrochloric acid and 400 ml of demineralized water is added over 15 minutes. After agitation for 2 hours at 20–22° C., then cooling down to 0° C., the crystals formed are separated out, washed with demineralized water, and dried under reduced pressure at 40° C. in order to obtain 171.7 g of the expected 3,4-dimethoxy 5-[[(4-methylphenyl)-sulphonyl]oxy]phenyl]-cinnamic acid.

PREPARATION 3

9,10-Dimethoxy-8-hydroxy-2,3,5,6-tetrahydro-benz[e]azulen-4 (1H) -one

Stage A: 9,10-Dihydroxy-8-[[(4-methylphenyl)sulphonyl]oxy]-2,3,5,6-tetrahydro-benz[e]azulen-4(1H)-one 30 g of 2,3,5,6-tetrahydro-8,9,10-trihydroxy-benz[e]azulen-4(1H)-one obtained according to Preparation 1 or 1a, 300 ml of tetrahydrofuran, 60 ml of triethylamine and 12.9 ml of trimethylborate are agitated for one hour 30 minutes at 20° C.±2° C. 30 g of tosyl chloride is added and agitation is carried out for 16 hours at 20° C.±2° C. then for 10 minutes at 20° C.±2° C., the reaction medium is poured into an agitated mixture of 900 ml of demineralized water and 150 ml of concentrated hydrochloric acid, then 90 ml of tetrahydrofuran and 60 ml of methylene chloride are added. The solution obtained is agitated for one hour at 20° C., then 150 ml of methylene chloride is introduced and agitation is continued for 15 minutes, followed by decanting and reextraction with 2×75 ml of methylene chloride. The combined organic phases are washed with 4×150 ml of demineralized water and reextracted with 75 ml of methylene chloride, after concentration under a reduced pressure of 20 mbars until distillation has stopped at 50° C., in order to obtain 47.6 g of the sought product.

Stage B: 9,10-Dimethoxy-8-[[(4-methylphenyl)sulphonyl]oxy]-2,3,5,6-tetrahydro-benz[e]azulen-4(1H)-one 47.6 g of the product obtained above, 300 ml of methylene chloride, 300 ml of soda (2N), 0.6 g of tetrabutylammonium bromide and 30 ml of dimethyl sulphate are agitated for 16 hours at 20° C. 30 ml of triethylamine is then introduced in order to destroy the excess dimethyl sulphate, the reaction medium is agitated for a further hour at 20° C.±2° C., then 150 ml of demineralized water is added, agitation is continued for 15 minutes followed by decanting. The aqueous phase is reextracted with 2×75 ml of methylene chloride and the combined organic phases are washed with 3×120 ml of demineralized water then 120 ml of N hydrochloric acid and 3×120 ml of demineralized water, the organic phases are combined and dried over sodium sulphate, then 120 g de silica gel (60 Mesh) is added over one hour at 20° C.±2° C. under agitation and agitation is carried out for a further one hour at 20° C., followed by filtration, washing with methylene chloride and concentrating to dryness under reduced pressure at 50° C. in order to obtain 47.4 g of the sought product. The crude product is purified by recrystallization from 390 ml of ethanol, after distillation of 90 ml of ethanol, agitation is carried out for 3 hours at 0° C.±2° C. The residue is separated off, washed with 30 ml of ethanol at 0° C., then dried under reduced pressure at 40° C. in order to obtain 41.1 g of the sought product (M.P.=129° C.).

Stage C: 9,10-Dimethoxy 8-Hydroxy 2,3,5,6-Tetrahydrobenz[e]-azulen-4 (1H) -one 4.5 g of potash then 10 ml of triethylamine are added to a suspension containing 10 g of 9,10-dimethoxy 8-(((4-methylphenyl)sulphonyl)oxy)2,3,5,6-tetrahydro-benz[e]azulen-4(1H)-one obtained as in Stage B and 100 ml of methanol. The reaction medium is heated under reflux for one hour, acidified by the addition of 20 ml of acetic acid then 20 ml of water is added. Extraction is carried out with dichloromethane, the extracts are washed with water, the solvent is evaporated off at 40° C. under reduced pressure and 5.7 g of expected product is collected.

PREPARATION 4

2,3,5,6-Tetrahydro-8-hydroxy-9-methoxy-benz[e]azulen-4 (1H)-one and 2,3,5,6-Tetrahydro-9-hydroxy-8-methoxy-benz[e]azulen-4(1H)-one The operation is carried out in an equivalent manner to Preparation 2 Stages B, C, D, E and F but starting with 3-(3,4-dimethoxy-phenyl)propionic acid and 1.08 g of crude product is obtained containing a mixture of monohydroxylated product (8-OH/9-OMe and 9-OH/8-OMe) which is separated by chromatography on silica using a cyclohexane/ethyl acetate mixture (7/3) as eluant. In this way the following two regioisomers are obtained:

8-OH/9-OMe 0.494 g Rf (cyclohexane/ethyl acetate 6/4)= 0.42

8-OMe/9-OH 0.041 g Rf (cyclohexane/ethyl acetate 6/4)= 0.33.

PREPARATION 5

2,3,5,6-tetrahydro-8-hydroxy-10-methoxy-benz[e]azulen-4(1H)-one and 2,3,5,6-Tetrahydro-10-hydroxy-8-methoxy-benz[e]azulen-4(1H)-one The operation is carried out in an equivalent manner to Preparation 2 Stages B, C, D, E and F but starting with 3-(3,5-dimethoxy-phenyl)propionic acid, and 1.428 g of a product is obtained containing a mixture of monchydroxylated products (8-OH/10-OMe and 10-OH/8-OMe) and dihydroxylated products (8-OH/10-OH), which are separated by chromatography on silica using a cyclohexane/ethyl acetate mixture (7/3).

PREPARATION 6

2,3,5,6-Tetrahydro-9-hydroxy-benz[e]azulen-4(1H)-one

The operation is carried out in an equivalent manner to Preparation 2 Stages B, C, D, E and F but starting with of 3-(4-methoxy-phenyl)propionic acid, and 0.448 g of expected product is obtained. Demethylation is carried out using boron tribromide.

(Rf=0.15 cyclohexane/ethyl acetate 7/3).

PREPARATION 7

2,3,5,6-Tetrahydro-8-hydroxy-benz[e]azulen-4(1)-one

The operation is carried out in an equivalent manner to Preparation 2 Stages B, C, D, E and F but starting with 10.0 g of 3-(3-methoxy-phenyl propionic acid, and 2.9 g of expected product is obtained. Demethylation is carried out using boron tribromide.

(Rf=0.15 dichloromethane/ethyl acetate 95/5).

PREPARATION 8

Methyl Ester of (DL)-4-Bromo 2-(Phenylmethoxycarbonylamino)butanoic Acid 25 g of 2-amino 4-butyrolactone hydrobromide in 200 ml of acetic acid with 24% gaseous hydrobromic acid is agitated for 18 hours at 120° C. in a closed chamber. The reaction medium is cooled down to ambient temperature, returned to atmospheric pressure, concentrated under reduced pressure, the residue is taken up in 200 ml of methanol then a current of hydrochloric acid is bubbled through for 2 hours while keeping the temperature below 35° C. The solvent is evaporated off under reduced pressure and the methyl ester of 2-amino 4-bromo butanoic acid is obtained which is taken up in 250 ml of acetone and 100 ml of water, the solution is neutralized using 2N soda then 35 ml of benzyl chloroformate is slowly added. Agitation is carried out for 48 hours, followed by filtration, extraction with ethyl acetate, the solvent is evaporated off, the residue is chromatographed on silica (eluant: cyclohexane-ethyl acetate 7-3) and 27.9 g of expected product is recovered. M.p.=90° C.

PREPARATION 9

Methyl Ester of 4-Bromo 2-(Terbutoxycarbonylamino)butanoic Acid 5.7 g of the methyl ester of 2-amino 4-bromo butanoic acid prepared as in Preparation 8 is agitated for 48 hours at ambient temperature in 120 ml of methanol with 24 ml of triethylamine and 9 g of diterbutyl dicarbonate. The solvents are evaporated off, the residue is taken up in water and dichloromethane, followed by filtration, extraction with dichloromethane, the solvents are evaporated off, the residue is chromatographed on silica (eluant: cyclohexane-ACOEt-TEA 7-3-0.5) and 1.575 g of expected product is obtained, Rf=0.52.

PREPARATION 10

4-(3-Pyrimidinyl) 1H-Imidazol 1-Propanol 505 mg of sodium ethylate is mixed with 12.5 ml of dimethylformamide, 1 g of 3-(1H-imidazol-4-yl)pyridine then 0.64 ml of chloropropanol are added and agitation is carried out for 16 hours at 55° C. The solvent is evaporated off under reduced pressure, the residue is chromatographed (eluant: $CH_2Cl_2$-MeOH 98-2) and 1.015 g of expected product is recovered. IR Spectrum ($CHCl_3$); OH 3626 $cm^{-1}$+associated; heterocycle 1601, 1578, 1551, 1499 $cm^{-1}$.

PREPARATION 11

Hexahydro-2H-1,3-diazepin-2-one Hydrazone

A suspension containing 3.3 g of nitroguanidine, 7 ml of water, 3.47 g of potash and 5 g of diamine dihydrochloride is heated at 65°–70° C. for one hour; 10.5 g of zinc is added, agitation is carried out for 30 minutes at ambient temperature, then 2 ml of acetic acid is added, the whole is heated for one hour at 40° C., followed by filtration and the addition of 3 g of ammonium chloride then 4 g of sodium bicarbonate. Extraction is carried out with dichloromethane, the solvent is evaporated off under reduced pressure, the residue is chromatographed on silica (eluant: $CH_2Cl_2$-MeOH-$NH_4OH$ 8-4-2) and 1.650 g of expected product is recovered.

PREPARATION 12

3a,4,5,6,7,7a-Hexahydro 2-(Propylthio) 1H-Benzimidazole Monohydrobromide 1 g of octahydro 2H-benzimidazol-2-thione and 1.3 ml of bromopropane in 20 ml of ethanol are heated under reflux until complete dissolution is obtained. The solvent is evaporated off under reduced pressure, the residue is taken up in a minimum amount of dichloromethane, isopropyl ether is added, the solvents are evaporated off under reduced pressure, the residue is recrystallized from isopropyl ether, the expected product is separated off and dried with a yield of 95%.

M.p.=136° C.

EXAMPLE 1

7-((4-(((Amino)iminomethyl)hydrazono)-9,10-dimethoxy-1,2,3,4,5,6-hexahydrobenz(e)azulen-8-yl)oxy)-heptanoic Acid Stage A: Methyl Ester of 7-(4-oxo)-9,10-Dimethoxy-1,2,3,4,5,6-hexahydrobenz(e)azulen-8-yl)oxy)-heptanoic Acid A suspension containing 0.684 g of 2,3,5,6-tetrahydro-8-hydroxy-9,10-dimethoxy-benz[e]azulen-4(1H)-one (Preparation 3), 12 ml of dimethylformamide (DMF), 12 ml of tetrahydrofuran (THF), 0.7 g of potassium carbonate and 0.835 g of methyl 7-bromo oenanthate is agitated at 40° C. for 4 hours. After evaporation under reduced pressure, the crude product is chromatographed on silica, eluting with a methylene chloride ($CH_2Cl_2$)/acetone mixture (95/5). In this way 1.000 g of purified product is obtained in the form of a yellow oil.

Rf $CH_2Cl_2$/acetone 95/5:0.5

IR ($CHCl_3$)

C=O 1732 $cm^{-1}$

OMe 1438 $cm^{-1}$ conjugated ketone 1641 $cm^{-1}$

C=C 1592 $cm^{-1}$, 1557 $cm^{-1}$, 1492 $cm^{-1}$+aromatic

Stage B: Methyl Ester of 7-((4-(((Amino)iminomethyl)hydrazono)-9,10-dimethoxy-1,2,3,4,5,6-hexahydro-benz(e)azulen-8-yl)oxy)-heptanoic Acid A suspension of 0.5 g of the product of the preceding Stage A, 5 ml of ethanol and 0.330 g of amino guanidine hydrochloride is agitated for 48 hours at ambient temperature, the solvent is evaporated off under reduced pressure and the crude product is purified by chromatography on silica, eluting with a $CH_2Cl_2$/methanol (MeOH)/ammonium hydroxide mixture (80/20/4). In this way 0.466 g of purified product is obtained in the form of a white foam.

Rf $CH_2Cl_2$/methanol (MeOH)/ammonium hydroxide 80/20/4:0.8

IR (Nujol)

NH/$NH_2$ 3495 $cm^{-1}$, 3155 $cm^{-1}$+associated

C=O 1731 $cm^{-1}$

C=N 1674 $cm^{-1}$

C=C 1625 $cm^{-1}$ aromatic 1595 $cm^{-1}$ (F)

NH/$NH_2$ 1534 $cm^{-1}$, 1491 $cm^{-1}$

Stage C: 7-((4-(((Amino)iminomethyl)hydrazono)-9,10-dimethoxy-1,2,3,4,5,6-hexahydrobenz(e)azulen-8-yl)oxy)-heptanoic Acid A solution containing 0.44 g of the product obtained in the preceding stage, 5 ml of ethanol and 2 ml of 1N soda is agitated for 3 hours at ambient temperature, then it is neutralized with 2 ml of 1N hydrochloric acid. After evaporation under reduced pressure, the crude product is purified by chromatography on silica, eluting with a $CH_2Cl_2$/methanol (MeOH)/ammonium hydroxide mixture (80/20/4). In this way 0.192 g of purified product is obtained, recrystallized from methanol.

Rf $CH_2Cl_2$/methanol (MeOH)/ammonium hydroxide 80/20/4: 0.17

NMR (D$_2$O+1 drop of 1N soda)
3.92 wt 2H C$\underline{H}_2$—O
2.17 t 2H C$\underline{H}_2$—COOH
1.34 m 4H
1.55 m 2H central CH$_2$'s+CH$_2$—C≡
1.70 m 4H
2.50 to 2.90 m 8H
6.62 s 1H aromatic H$_7$
3.64 s 3H OCH$_3$
3.73 s 3H OCH$_3$
Microanalysis

| % calculated | C 62.86 | H 7.47 | N 12.21 |
| --- | --- | --- | --- |
| % found | C 62.9 | H 7.5 | N 12.1 |

By operating in an equivalent manner to Example 1, Stages A, B and C, starting with 2,3,5,6-tetrahydro-8-hydroxy-9,10-dimethoxy-benz[e]azulen-4(1H)-one (Preparation 3), but with different alkylating groups and G-NH$_2$ groups, the following products of formula (I) were prepared:

EXAMPLE 2

4-((4-(((Amino)iminomethyl)hydrazono)-9,10-dimethoxy-1,2,3,4,5,6-hexahydrobenz(e)azulen-8-yl)oxy)-butanoic Acid

EXAMPLE 3

4-((4-(((Amino)iminomethyl)hydrazono)-9,10-dimethoxy-1,2,3,4,5,6-hexahydrobenz(e)azulen-8-yl)oxy)-pentanoic Acid

EXAMPLE 4

5-((4-(((Amino)carbonyl)hydrazono)-9,10-dimethoxy-1,2,3,4,5,6-hexahydro-8-benz(e)azulenyl)oxy)-pentanoic Acid

EXAMPLE 5

6-((4-(((Amino)iminomethyl)hydrazono)-9,10-dimethoxy-1,2,3,4,5,6-hexahydro-8-benz(e)azulenyl)oxy)-hexanoic Acid

EXAMPLE 6

5-(9,10-dimethoxy-1,2,3,4,5,6-hexahydro-4-(4,5-dihydro-1H-imidazolin-2-yl)hydrazono)-8-benz(e)azulenyl)oxy)-pentanoic Acid

EXAMPLE 7

5-((4-(((Amino)thiocarbonyl)hydrazono)-9,10-dimethoxy-1,2,3,4,5,6-hexahydro-8-benz(e)azulenyl)oxy)-pentanoic Acid

EXAMPLE 8

6-(4((4,5-Dihydro-1H-imidazolin-2-yl)hydrazono)-9,10-dimethoxy-1,2,3,4,5,6-hexahydro-8-benz(e)azulenyl)oxy)-hexanoic Acid

EXAMPLE 9

5-((4-(((Amino)iminomethyl)hydrazono)-9,10-dimethoxy-1,2,3,4,5,6-hexahydro-8-benz(e)azulenyl)oxy)-3,3-dimethyl-4-oxo-pentanoic Acid

EXAMPLE 10

5-(4((4,5-Dihydro-1H-imidazolin-2-yl)hydrazono)-9,10-dimethoxy-1,2,3,4,5,6-hexahydro-S-benz(e)azulenyl)oxy)-3,3-dimethyl-4-oxo-pentanoic Acid

EXAMPLE 11

4-(4((4,5-Dihydro-1H-imidazolin-2-yl)hydrazono)-9,10-dimethoxy-1,2,3,4,5,6-hexahydro-8-benz(e)azulenyl)oxy)-butanoic Acid

EXAMPLE 12

4-((9,10-Dimethoxy-4-((1,4,5,6-tetrahydro-2-pyrimidinyl)hydrazono)-1,2,3,4,5,6-hexahydro-8-benz(e)-azulenyl)oxy)-butanoic Acid

EXAMPLE 13

2-(4((4,5-Dihydro-1H-imidazolin-2-yl)hydrazono)-9,10-dimethoxy-1,2,3,4,5,6-hexahydro-8-benz(e)azulenyl)oxy)-ethanoic Acid

EXAMPLE 14

3-(4((4,5-Dihydro-1H-imidazolin-2-yl)hydrazono)-9,10-dimethoxy-1,2,3,4,5,6-hexahydro-8-benz(e)azulenyl)oxy)-propanoic Acid

| Ex. | Starting product | Alkylating product | G-NH₂ | Rf. (1) |
|---|---|---|---|---|
| 2 | P3 | Br—(CH₂)₃—CO₂Et | H₂N—NH—C(=NH)—NH₂.HCl | 0, 12 |
| 3 | P3 | Br—(CH₂)₄—CO₂Et | H₂N—NH—C(=NH)—NH₂.HCl | 0, 12 |
| 4 | P3 | Br—(CH₂)₃—CO₂Et | H₂N—NH—C(=O)—NH₂.HCl | 0, 18 |
| 5 | P3 | Br—(CH₂)₅—CO₂Et | H₂N—NH—C(=NH)—NH₂.HCl | 0, 17 |
| 6 | P3 | Br—(CH₂)₄—CO₂Et | H₂N—NH—C(=N—CH₂CH₂—NH) (cyclic amidine) .HBr | 0, 27 |
| 7 | P3 | Br—(CH₂)₄—CO₂Et | H₂N—NH—C(=S)—NH₂.HCl | 0, 25 |
| 8 | P3 | Br—(CH₂)₅—CO₂Et | H₂N—NH—C(=N—CH₂CH₂—NH) (cyclic amidine) .HBr | 0, 6 |
| 9 | P3 | BrCH₂C(O)C(Me)₂—CH₂CO₂Et | H₂N—NH—C(=NH)—NH₂.HCl | 0, 3 |
| 10 | P3 | BrCH₂C(O)C(Me)₂—CH₂CO₂Et | H₂N—NH—C(=N—CH₂CH₂—NH) (cyclic amidine) .HBr | 0, 5 |
| 11 | P3 | Br—(CH₂)₃—CO₂Et | H₂N—NH—C(=N—CH₂CH₂—NH) (cyclic amidine) .HBr | 0, 3 |
| 12 | P3 | Br—(CH₂)₃—CO₂Et | H₂N—NH—C(=N—CH₂CH₂—NH) (cyclic amidine) .HBr | 0, 63 |
| 13 | P3 | Br—(CH₂)—CO₂Et | H₂N—NH—C(=N—CH₂CH₂—NH) (cyclic amidine) .HBr | 0, 3 |
| 14 | P3 | Br—(CH₂)₂—CO₂Et | H₂N—NH—C(=N—CH₂CH₂—NH) (cyclic amidine) .HBr | 0, 22 |

(1) dichloromethane/methanol/ammonium hydroxide 80/20/4

EXAMPLE 15

5-((4-(((Amino)iminomethyl)hydrazono)-9,10-dimethoxy-1,2,3,4,5,6-hexahydrobenz(e)azulen-8-yl)oxy)-pentanoic Acid Hydrochloride 86 mg of the product of Example 3 is mixed with 2 ml of water and 4 1 of 0.1N hydrochloric acid then after a few minutes, the medium is lyophilized. 91 mg of expected salt is obtained.

EXAMPLE 16

4-((4-(((Amino)iminomethyl)hydrazono)-8,9-dimethoxy-1,2,3,4,5,6-hexahydro-10-benz(e)azulenyl)oxy)-butanoic Acid

EXAMPLE 17

5-((4-(((Amino)iminomethyl)hydrazono)-8,9-dimethoxy-1,2,3,4,5,6-hexahydro-10-benz(e)azulenyl)oxy)-pentanoic Acid The operation is carried out as in Example 1 Stages A, B and C, but starting with 2,3,5,6-tetrahydro-10-hydroxy-8,9-dimethoxy-benz[e]azulen-4(1H)-one (Preparation 2).

| Ex. | Starting product | Alkylating product | G—NH₂ | Rf. |
|---|---|---|---|---|
| 16 | (II)ₐ | Br—(CH₂)₃—CO₂Et | H₂N—NH—C(=NH)—NH₂.HCl | 0,07 |

-continued

| Ex. | Starting product | Alkylating product | G—NH$_2$ | Rf. |
|---|---|---|---|---|
| 17 | (II)$_A$ | Br—(CH$_2$)$_4$—CO$_2$Et | H$_2$N—NH—C(=NH)—NH$_2$.HCl | 0,07 |

EXAMPLE 18

4-((4-(((Amino)iminomethyl)hydrazono)-8,10-dimethoxy-1,2,3,4,5,6-hexahydro-9-benz(e)azulenyl)oxy)-butanoic Acid

EXAMPLE 19

5-((4-(((Amino)iminomethyl)hydrazono)-8,10-dimethoxy-1,2,3,4,5,6-hexahydro-9-benz(e)azulenyl)oxy)-pentanoic Acid The operation is carried out as in Example 1 Stages A, B and C, but starting with 2,3,5,6-tetrahydro-9-hydroxy-8,10-dimethoxy-benz[e]azulen-4(1H)-one.

| Ex. | Starting product | Alkylating product | G—NH$_2$ | Rf. |
|---|---|---|---|---|
| 18 | (II)$_A$ | Br—(CH$_2$)$_3$—CO$_2$Et | H$_2$N—NH—C(=NH)—NH$_2$.HCl | 0,10 |
| 19 | (II)$_A$ | Br—(CH$_2$)$_4$—CO$_2$Et | H$_2$N—NH—C(=NH)—NH$_2$.HCl | 0,07 |

EXAMPLE 20

4-((4((4,5-Dihydro-1H-imidazol-2-yl)hydrazono)-1,2,3,4,5,6-hexahydro-9-benz(e)azulenyl)oxy)-butanoic Acid Stage A: Ethyl Ester of 4-(4-oxo)-1,2,3,4,5,6-Hexahydrobenz(e)azulen-9-yl)oxy)-butanoic Acid A suspension containing 0.6 g of 2,3,5,6-tetrahydro-9-hydroxy-benz[e]azulen-4(1H)-one (Preparation 6), 12 ml of dimethylformamide (DMF), 12 ml of tetrahydrofuran (THF), 0.7 g of potassium carbonate and 0.7 ml of ethyl bromobutyrate is agitated at ambient temperature overnight. After evaporation under reduced pressure the crude product is chromatographed on silica, eluting with a methylene chloride mixture (dichloromethane/acetone 95/5). In this way 0.608 mg of purified product is obtained in the form of a yellow oil.

IR (CHCl$_3$)

C=O 1728 cm$^{-1}$ conj. ketone 1641 cm$^{-1}$

Aromatic C=C's 1610 cm$^{-1}$, 1590 cm$^{-1}$ 1569 cm$^{-1}$, 1499 cm$^{-1}$

Stage B: Ethyl Ester of 4-((4-((4,5-Dihydro-1H-imidazolin-2-yl)hydrazono)-1,2,3,4,5,6-hexahydrobenz(e)azulen-9-yl)oxy)-butanoic Acid 608 mg of the product of the preceding Stage A, 10 ml of butanol and 600 mg of the following cyclic amino guanidine hydrobromide: (4,5-dihydro-1H-imidazolin-2-yl)-hydrazine, are agitated under reflux for 24 hours, the solvent is evaporated off under reduced pressure and the crude product is purified by chromatography on silica, eluting with a CH$_2$Cl$_2$/methanol (MeOH)/ammonium hydroxide mixture (80/20/4). In this way 0.604 g of expected product is obtained.

IR (CHCl$_3$)

=C—NH— 3451 cm$^{-1}$

C=O 1728 cm$^{-1}$ (ester)

C=N+C=C+aromatics: 1627 cm$^{-1}$ (F), 1568 cm$^{-1}$ 1548 cm$^{-1}$, 1497 cm$^{-1}$, 1488 cm$^{-1}$ Stage C: 7-((4,5-Dihydro-1H-imidazolin-2-yl)hydrazono)-1,2,3,4,5,6-hexahydrobenz(e)azulen-9-yl)oxy)-butanoic acid A solution containing 0.604 g of the product obtained in the preceding stage, 8 ml of ethanol, 5 ml of tetrahydrofuran and 2 ml of 2N soda is agitated for 4 hours at ambient temperature, then it is neutralized with 2 ml of hydrochloric acid. After evaporation under reduced pressure, the crude product is purified by chromatography on silica, eluting with a dichloromethane (CH$_2$Cl$_2$)/methanol (MeOH)/ammonium hydroxide mixture (80/20/4). In this way 0.298 g of purified product is obtained, recrystallized from methanol.

Rf (dichloromethane/methanol/ammonium hydroxide 80/20/4): 0.2

NMR (D$_2$O+1 drop of 1N soda)

| 1.71 (w) 2 H | O—CH$_2$—CH$_2$—CH$_2$—CO |
|---|---|
| 1.96 (m) 2 H | CH$_2$ in position 2 (cyclopentene) |
| 2.30 (t) 2 H | CH$_2$—CO |
| 2.50 to 2.75 8 H | CH$_2$—C= |
| 3.45 (ws) 4 H | CH$_2$—N= |
| 3.89 (wt) 2 H | Ph—O—CH$_2$—C |
| 6.70 (m) 2 H | H$_{10}$ and H$_8$ |
| 7.00 (d, J = 8) | H$_7$ |

EXAMPLE 21

4-(4((4,5-Dihydro-1H-imidazolin-2-yl)hydrazono)-1,2,3,4,5,6-hexahydro-8-benz(e)azulenyl)oxy)-butanoic Acid The operation is carried out as in Example 20 but starting with 0.856 g of 2,3,5,6-tetrahydro-8-hydroxy-benz[e]azulen-4(1H)-one (Preparation 7) and 0.299 g of expected product is obtained.

Rf (dichloromethane/methanol/ammonium hydroxide 80/20/4):0.27.

EXAMPLE 22

5-((8-(((Amino)iminomethyl)hydrazono)-6,7,8,9,10,11-hexahydro-azuleno(5,6-d)-1,3-benzodioxol-4-yl)-oxy)-pentanoic Acid Stage A: Ethyl Ester of 5-(((4-oxo)-9,10-Dihydroxy-1,2,3,4,5,6-hexahydro-benz(e)azulen-9-yl)oxy)-pentanoic Acid 1) Protection 4.42 ml of trimethoxyborate and 20.4 ml of triethylamine are added to a solution, under an inert atmosphere, of 10 g of 2,3,5,6-tetrahydro-8,9,10-trihydroxy-benz[e]azulen-4(1H)-one (Preparation 1) in 100 ml of tetrahydrofurani while maintaining the temperature between 37 and 39° C., then the reaction medium is agitated at ambient temperature for 3 hours.

2) Alkylation and Deprotection

Next 9.7 ml of ethyl bromo-5-valerate, 100 ml of dimethylformamide and 8.4 g of potassium carbonate are added and agitation is carried out for 2 days at 60° C. The reaction ixture is then treated with 120 ml of water and 50 ml of 36N concentrated hydrochloric acid, agitation is carried out for one hour, ethyl acetate is added, the organic and aqueous phases are separated off. The organic phase is then washed, dried and evaporated under reduced pressure. A crude product is obtained which is purified by chromatography on silica, eluting with a cyclohexane/ethyl acetate mixture (70/30). 5.2 g of expected pure product is obtained.

Rf (dichloromethane/methanol 95/5)=0.82; Rf (cyclohexane/ethyl acetate 70/30)=0.23.

Stage B: Ethyl Ester of 5-(((8-oxo)-6,7,8,9,10,11-Hexahydro-azuleno(5,6-d)-1,3-benzodioxol-4-yl)oxy))-pentanoic Acid 2.5 g of the product obtained in the preceding stage, 17 ml of dimethylformamide, 3.6 g of CsF and 1.4 ml of dibromomethane are mixed together under an inert atmosphere at 60° C. for one hour. After filtration and rinsing with methanol, evaporation is carried out under reduced pressure and the crude product is purified by chromatography on silica, eluting with a cyclohexane/ethyl acetate mixture (85/15). 1.73 g of expected pure product is obtained. (M.P.= 118° C.)

Rf (cyclohexane/ethyl acetate 80/20)=0.25

Stage C: Ethyl Ester of 5-((8-(((Amino)iminomethyl)-hydrazono)-6,7,8,9,10,11-hexahydro-azuleno(5,6-d)-1,3-benzodioxol-4-yl)oxy)-pentanoic Acid 551 mg of the product obtained in the preceding stage and 467 mg of aminoguanidine hydrochloride are mixed together overnight at 120° C., then purification is carried out by chromatography, eluting with a dichloromethane/methanol/ammonium hydroxide mixture (80/20/4). 174 mg of the expected product is obtained.

Rf (dichloromethane/methanol/ammonium hydroxide 80/20/4) 0.98

Stage D: 5-((8-(((Amino)iminomethyl)hydrazono)-6,7,8,9,10,11-hexahydro-azuleno(5,6-d)-1,3-benzodioxol-4-yl)oxy)-pentanoic Acid 274 mg of the product obtained in the preceding stage and 1.86 ml of 1N soda are mixed together at ambient temperature for one hour 30 minutes, then the mixture is neutralized by a 1N hydrochloric acid solution, and evaporated under reduced pressure. The crude product is purified by chromatography, eluting with a dichloromethane/methanol/ammonium hydroxide mixture (80/20/4). 141 mg of the expected product is obtained.

Rf (dichloromethane/methanol/ammonium hydroxide 80/20/4) 0.23; NMR (DMSO)

1.55 to 1.9 (m) 4H O—$CH_2$—$CH_2$—$CH_2$—$CH_2$—CO 1.55 to 1.9 (m) 2H $CH_2$ in position 2 (cyclopentene)

2.26 (t) 2H $CH_2$—CO 2.65 to 3.00 (m) 8H $CH_2$—C=

4.07 (t) 2H O—$CH_2$—$CH_2$—

5.95 (s) 2H —O—$CH_2$—O 6.61 (m) 1H $H_8$ mobile H's (wide m) NH—C(=NH)—$NH_2$

EXAMPLE 23

5-((8-(((Amino)iminomethyl)hydrazono)-2,2-diphenyl-6,7,8,9,10,11-hexahydro-azuleno(4,5-e)-1,3-benzodioxol-4-yl)oxy)-pentanoic Acid The operation is carried out as in the preceding example, starting with 374 mg of the product obtained in Stage A of the preceding example and 0.19 ml of diphenyldichloromethane. 198 mg of expected product is obtained.

Rf (dichloromethane/methanol/ammonium hydroxide 80/20/4)=0.17

EXAMPLE 24

O-[4-[(4,5-dihydro-1H-imidazol-2-yl)hydrazono)-9,10-dimethoxy-1,2,3,4,5,6-hexahydro-8-benz(e) azulenyl]-N-[(phenylmethoxy)carbonyl]-DL-homoserine Stage A: Methyl Ester of O-[(4-oxo)-9,10-Dimethoxy-1,2,3,4,5,6-hexahydro-8-benz(e)azulenyl]-N-[(phenylmethoxy)-carbonyl]-DL-homoserine 0.6 g of 2,3,5,6-tetrahydro-8-hydroxy-9,10-dimethoxy-benz[e]azulen-4(1H)-one (Preparation 3), 10 ml of dimethylformamide (DMF), 10 ml of tetrahydrofuran, 1 g of potassium carbonate and 0.867 g of methyl ester of (DL)-4-bromo-2-(phenylmethoxycarbonylamino)butanoic acid prepared as indicated in preparation 8 are agitated overnight at ambient temperature. After evaporation under reduced pressure, the crude product is chromatographed on silica, eluting with a methylene chloride ($CH_2Cl_2$)/acetone mixture (95/5). In this way 1.166 g of purified product is obtained in the form of a yellow oil.

IR ($CHCl_3$)

C=O 1740 $cm^{-1}$ (sh.), 1721 $cm^{-1}$ conj. ketone 1642 $cm^{-1}$

Aromatic C=C's 1593 $cm^1$, 1559 $cm^{-1}$, 1508 $cm^{-1}$, 1493 $cm^{-1}$

Stage B: Methyl Ester of O-[4-[(4,5-Dihydro-1H-imidazol-2-yl)hydrazono)-9,10-dimethoxy-1,2,3,4,5,6-hexahydro-8-benz-(e)azulenyl]-N-[(phenylmethoxy)carbonyl]-DL-homoserine 539 mg of the product of the preceding Stage A, 15 ml of butanol and 600 mg of the following cyclic amino guanidine hydrobromide: (4,5-dihydro-1H-imidazol-2-yl)-hydrazine, are agitated for 24 hours at 120° C., the solvent is evaporated off under reduced pressure, and the crude product is purified by chromatography on silica, eluting with a $CH_2Cl_2$/methanol (MeOH)/ammonium hydroxide mixture (80/20/4). In this way 0.641 g of expected product is obtained.

IR ($CHCl_3$)

=C—NH— 3451 $cm^{-1}$+associated

C=O 1740 $cm^{-1}$ (sh.), 1720 $cm^{-1}$ (max)

C=N+C=C+aromatics+amide II: 1667 $cm^{-1}$ (F), 1606 $cm^{-1}$, 1508 $cm^{-1}$, 1490 $cm^{-1}$.

Stage C: O-[4-[(4,5-Dihydro-1H-imidazol-2-yl)hydrazono)-9,10-dimethoxy-1,2,3,4,5,6-hexahydro-8-benz(e)azulenyl]-N-[(phenylmethoxy)carbonyl]-DL-homoserine.

A solution containing 0.6 g of the product obtained in the preceding stage, 10 ml of ethanol and 2 ml of 2N soda is agitated for 2 hours at ambient temperature, then it is neutralized with 2 ml of hydrochloric acid. After evaporation under reduced pressure, the crude product is purified by chromatography on silica, eluting with a $CH_2Cl_2$/methanol (MeOH)/ammonium hydroxide mixture (80/20/4). In this way 0.349 g of purified product is obtained, recrystallized from methanol.

Rf $CH_2Cl_2$/methanol (MeOH)/ammonium hydroxide 80/20/4: 0.37

EXAMPLE 25

O-[4-[(4,5-Dihydro-1H-imidazol-2-yl)hydrazono)-1,2,3,4,5,6-hexahydro-8-benz(e)azulenyl]-N-[(phenylmethoxy)-carbonyl]-DL-homoserine The operation is carried out in an equivalent manner to Example 24 but starting with 0.428 g of 2,3,5,6-tetrahydro- 9-hydroxy-benz[e]azulen-4(1H)-one (Preparation 7). 245 mg of expected product is obtained.

Rf CH$_2$Cl$_2$/methanol (MeOH)/ammonium hydroxide 80/20/4: 0.5

EXAMPLE 26

O-[4-[(1,2,3,4-tetrahydro 6-pyrimidinyl)hydrazono] 9,10-dimethoxy 1,2,3,4,5,6-hexahydro8-benz[e]-azulenyl]N-[(phenylmethoxy)carbonyl]DL-homoserine Stage A: Monohydrobromide of the Methyl Ester of O-[9,10-Dimethoxy1,2,3,4,5,6-hexahydro4-[(1,4,5,6-tetrahydro2-pyrimidinyl)hydrazono]8-benz(e)azulenyl]N-[(phenylmethoxy)carbonyl]DL-homoserine.

The operation is carried out as in Example 24 Stage B starting with 200 mg of the product obtained as in Example 24 Stage A in 2 ml of butanol and 74.5 mg of tetrahydro-2 (1H)-pyrimidinone hydrazone monohydrobromide and heating under reflux for 16 hours. The reaction medium is allowed to return to ambient temperature, extraction is carried out with dichloromethane, the extracts are dried, the solvent is evaporated off under reduced pressure and 152 mg of expected product is obtained.

Stage B: O-[4-[(1,2,3,4-Tetrahydro6-pyrimidinyl) hydrazono]9,10-dimethoxy1,2,3,4,5,6-hexahydro8-benz[e] azulenyl]N-(phenylmethoxy)carbonyl]DL-homoserine.

The operation is carried out as in Example 24 Stage C using 131 mg of product obtained in Stage A above in solution in 1.3 ml of ethanol and 0.43 ml of N soda. The reaction medium is neutralized by the addition of N hydrochloric acid, the solvent is evaporated off, and after filtration and drying, 78 mg of expected product is obtained. M.p. =172° C.

NMR Spectrum (CDCl$_3$).

| | |
|---|---|
| 1.90 (m) (2 H) | CH$_2$ in position 9 |
| 2.03 (m) | central CH$_2$ |
| 2.36 (m) (2 H) | |
| 2.60 to 3.00 (8 H) | the =C—CH$_2$'s |
| 3.48 (wm) (4 H) | the =N—CH$_2$'s |
| 3.77 (s) 3.78 (s) (9 H) | the =C—OMe's |
| 4.01 (m) (1 H) 4.17 | Φ—O—CH$_2$ |
| 4.67 (p) | =C—CH—N—C= |
| 5.14 (ws) | COO—CH$_2$—Φ |
| 6.13 (d) | =C—NH—CH |
| 6.49 (ws) | H$_4$ |
| ≈7.36 (m) (5 H) | Φ—C |

EXAMPLE 27

(2,3-Dihydroxypropyl) Ester of O-(9,10-Dimethoxy1,2,3,4,5,6-hexahydro 4-[(1,4,5,6-tetrahydro2-pyrimidinyl)hydrazono]-8-benz(e) azulenyl]N-[(phenylmethoxy)carbonyl]DL-homoserine.

Stage A: [(2,2-Dimethyl1,3-Dioxolan-4-yl)methyl] Ester of O-[9,10-dimethoxy1,2,3,4,5,6-hexahydro4-[(1,4,5,6-tetrahydro-2-pyrimidinyl)hydrazono]8-benz(e)azulenyl)N-[(phenyl-methoxy)carbonyl]DL-homoserine.

0.3 g of product prepared as in Example 26 in 1 ml of dimethylformamide and 1 ml of dichloromethane, 96 mg of 1-(3-dimethylaminopropyl) 3-ethylcarbodiimide hydrochloride and 68 mg of 1-hydroxy benzotriazole hydrate are cooled down to 0° C. The mixture is agitated for 30 minutes at ambient temperature, 0.06 ml of solketal is introduced and agitation is continued for 3 hours and 30 minutes. The reaction medium is diluted with water, extraction is carried out with dichloromethane and 0.6 g of crude product is recovered which is purified by chromatography on silica (eluant: CHCl$_2$-MeOH 90-10). 0.352 g of expected product is obtained.

IR Spectrum (CHCl$_3$)

| | |
|---|---|
| NH | 3400 cm$^{-1}$ |
| C=O | 1745 (sh), 1719 cm$^{-1}$ |

C=N, C=C} aromatic, amide II} 1672 (F), 1645, 1597, 1565 (f), 1507, 1492 cm$^{-1}$

Stage B: (2,3-dihydroxypropyl) Ester of O-(9,10-Dimethoxy 1,2,3,4,5,6-hexahydro4-[(1,4,5,6-tetrahydro2-pyrimidinyl) hydrazono]-8-benz(e)azulenyl]N-[(phenylmethoxy) carbonyl]DL-homoserine.

0.320 g of product obtained in Stage A is agitated for 6 hours at ambient temperature in 3 ml of ethanol and 1 ml of 2N hydrochloric acid. After evaporation of the solvents and chromatography on silica (eluant: CH$_2$Cl$_2$-MeOH-NH$_4$OH 80-20-4), 0.112 g of expected product is obtained.

NMR Spectrum (CDCl$_3$)

| | |
|---|---|
| 1.88 (m) (2 H) | } |
| 1.98 } | central CH$_2$'s and CH$_2$ in position 9 |
| 2.36 } | |
| 2.60 to 3.10 (8 H) | =C—CH$_2$ |
| 3.43 (m) (4 H) | =N—N—CH$_2$ |
| 3.79 (s) | } |
| 3.81 } | Φ—OMe |
| 3.60 to 3.90 | O—CH$_2$—CH—O |
| ≈4.00 to 4.30 } | COO—CH$_2$—CH |
| } | Φ—O—CH$_2$—CH$_2$ |
| 4.64 (m) (1 H) | =C—CH—N—C= |
| 5.13 (s) | COO—CH$_2$—Φ |
| 6.53 (s) | H$_4$ |
| 7.20 to 7.38 | the Φ—C's |

EXAMPLE 28

O-[4-[(4,5-Dihydro1H-imidazol-2-yl)hydrazono]9, 10-dimethoxy 1,2,3,4,5,6-hexahydro8-benz(e) azulenyl]N-[(8-quinolinyl)sulphonyl]DL-homoserine Stage A: Methyl Ester of O-(9,10-Dimethoxy1,2,3,4,5,6-hexahydro 4-oxo8-benz(e)azulenyl)N-[(1,1-dimethylethoxy)carbonyl]DL-homoserine.

4.1 g of product prepared as in Preparation 3 and 5 g of the ester prepared as in Preparation 9 are agitated at ambient temperature for 65 hours in 50 ml of dimethylformamide and 50 ml of tetrahydrofuran in the presence of 5 g of potassium carbonate and dimethylaminopyridine. The solvent is evaporated off under reduced pressure, the residue is purified by chromatography on silica (eluant: CH$_2$Cl$_2$-acetone 95-5) and 7.3 g of expected product is recovered.

IR Spectrum (CHCl$_3$)

| | |
|---|---|
| =C—NH | 3430 cm$^{-1}$ |
| C=O | 1744 cm$^{-1}$ (methyl ester) |
| | 1710 cm$^{-1}$ (NH—BOC) |
| | 1648 cm$^{-1}$ (conjugated ketone) | aromatic+amide II 1593, 1559, 1493 cm$^{-1}$.

Stage B: Monohydrochloride of Methyl Ester of O-(9,10-Dimethoxy1,2,3,4,5,6-hexahydro4-oxo8-benz(e)azulenyl) DL-homoserine.

10 ml of hydrochloric acid in ethyl acetate is added in three lots to 6 g of product prepared in Stage A in 10 ml of ethyl acetate then agitation is carried out for 16 hours at ambient temperature. The solvent is evaporated off under reduced pressure and 0.656 g of expected product is obtained which is used as it is for the following stage.

Stage C: O-(9,10-Dimethoxy1,2,3,4,5,6-hexahydro4-oxo8-benz(e)azulenyl)N-[(8-quinolinyl)sulphonyl]DL-homoserine.

0.656 g of the product obtained above is taken up in 5 ml of dichloromethane, 1 ml of triethylamine and 0.638 g of 8-chlorosulphonyl quinoline are added and agitation is carried out for 2 hours at ambient temperature. After evaporation of the solvents under reduced pressure and chromatography on silica (eluant: $CHCl_2$-MeOH 95-5), 0.956 g of expected product is recovered.

Stage D: Methyl Ester of O-[4-[(4,5-Dihydro1H-imidazol-2-yl)hydrazono]9,10-dimethoxy1,2,3,4,5,6-hexahydro8-benz(e)azulenyl] N-[(8-quinolinyl)sulphonyl]DL-homoserine.

0.9 g of the product of the preceding Stage A, 5 ml of butanol and 0.6 g of the following cyclic aminoguanidine hydrobromide: (4,5-dihydro1H-imidazol-2-yl)hydrazine, are agitated for 16 hours at 120° C., the solvent is evaporated off under reduced pressure and 0.786 g of expected product is obtained, used as it is for the following stage.

Stage E: O-[4-[(4,5-dihydro1H-imidazol-2-yl)hydrazono]9,10-dimethoxy1,2,3,4,5,6-hexahydro8-benz(e)azulenyl]N-[(8-quinolinyl)sulphonyl]DL-homoserine.

The solution containing 0.786 g of the product obtained in the preceding stage, 5 ml of methanol and 2 ml of 2N soda is agitated for 2 hours at ambient temperature, then neutralized with 2 ml of 2N hydrochloric acid and agitation is continued for 10 minutes. After evaporation under reduced pressure, the crude product is purified by chromatography on silica, eluting with a $CH_2Cl_2$-methanol-ammonium hydroxide mixture (80-20-4). 0.438 g of expected product is obtained after recrystallization from methanol.

Rf=0.40 ($CHCl_2$-MeOH-$NH_4OH$ 80-20-4).

NMR Spectrum (DMSO)

| | |
|---|---|
| 1.81 (ws) | $CH_2$ in position 9 |
| 2.40 to 3.20 | the $=C-CH_2$'s |
| 3.35 (w) | the $=N-CH_2$'s |
| 3.55 (ws) | the $=C-OMe$'s |
| 6.63 (ws) | $H_4$ |
| 7.58 (dd) | $H'_3$ |
| 7.67 (t) | $H'_6$ |
| 8.19 (d), 8.29 (d) | $H'_5$ and $H'_7$ |
| 8.45 (d) | $H_4$ |
| 8.90 (d) | $H_2$ |
| 7.31 (ws) | } |
| 7.97 | }mobile H's |
| 10.40 (f) | } |
| 12.62 | } |

EXAMPLE 29

Monohydrochloride of O-[4-[(4,5-Dihydro1H-imidazol-2-yl)hydrazono]9,10-dimethoxy1,2,3,4,5,6-hexahydro8-benz(e)azulenyl]N-[[3-[4-(3-pyridinyl)1H-imidazol-1-yl]propoxy]carbonyl]DL-homoserine

Stage A: Methyl 4-[[9,10-Dimethoxy1,2,3,4,5,6-hexahydro4-oxo8-benz(e)azulenyl)oxy]2-isocyanato Butanoate.

450 mg of the amine obtained in Stage B of Example 28 is agitated for 10 minutes at 0° C. in 10.2 ml of a saturated aqueous solution of sodium bicarbonate and 10.2 ml of dichloromethane. 204 mg of triphosgene in solution in 2 ml of dichloromethane is added to the organic phase of the reaction medium, agitation is carried out for 10 minutes, followed by extraction with dichloromethane, the extracts are dried, the solvent is evaporated off under reduced pressure and 430 mg of expected product is obtained which is used as it is for the following stage.

Stage B: O-[9,10-Dimethoxy1,2,3,4,5,6-hexahydro4-oxo8-benz(e)azulenyl]N-[[3-(4-(3-pyridinyl)1H-imidazol-1-yl]propoxy]carbonyl]DL-homoserine.

430 mg of the product obtained in Stage A in 20 ml of dichloromethane is cooled down to 0° C. and 414 mg of the alcohol prepared as in Preparation 10 in 10 ml of dichloromethane is added. The reaction medium is allowed to return to ambient temperature, maintained under agitation for 48 hours, the solvent is evaporated off under reduced pressure, the residue is chromatographed on alumina (eluant: $CH_2Cl_2$-MeOH) and 298 mg of expected product is recovered.

Stage C: Monohydrobromide of O-[4[(4,5-dihydro1H-imidazol-2-yl)hydrazono]9,10-dimethoxy1,2,3,4,5,6-hexahydro8-benz(e)-azulenyl]N-[[3-[4-(3-pyridinyl)1H-imidazol-1-yl)propoxy]carbonyl)DL-homoserine.

The operation is carried out as in Example 24 Stage B starting with 277 mg of the product obtained in Stage B above and 164 mg of cyclic aminoguanidine hydrobromide in 13 ml of butanol. After chromatography on alumina (eluant: $CH_2Cl_2$-MeOH 95-5), 289 mg of expected product is obtained.

IR-Spectrum ($CHCl_3$)

| | |
|---|---|
| C=O conjugated sys.}+ aromatic } | 1746 (sh) 1723 (max) $cm^{-1}$ |
| | 1668, 1625 (F), 1599 (sh), 1551, 1509, 1489 $cm^{-1}$ + amide II } |
| OH | 3618 $cm^{-1}$ |

Stage D: Monohydrochloride of O-(4-((4,5-Dihydro1H-imidazol-2-yl)hydrazono]9,10-dimethoxy1,2,3,4,5,6-hexahydro8-benz(e)azulenyl]N-[[3-[4-(3-pyridinyl)1H-imidazol-1-yl]propoxy]carbonyl]DL-homoserine.

0.3 ml of N soda is added to 277 mg of product obtained in Stage C above in 10 ml of ethanol, agitation is carried out for 30 minutes, 10 ml of water is added, the reaction medium is acidified to a pH of 2.5 using N hydrochloric acid, the solvents are evaporated off under reduced pressure, the residue is chromatographed on silica (eluant: $CH_2Cl_2$-MeOH-$NH_4OH$ 40-10-2), the filtrate is evaporated under reduced pressure, the residue is taken up in isopropyl ether, the precipitate is filtered off, dried and 126 mg of expected product is collected.

NMR Spectrum (DMSO)

| | |
|---|---|
| 1.78 (m) (2 H) } | |
| 1.90 to 2.30 (m) (5 H) } | the 3—$CH_2$'s |
| 1.60 to 2.90 (m) (8 H) | the $CH_2$—C = 's |
| 3.53 (ws) (≈4 H) | N—$CH_2$—$CH_2$—N |
| 3.69 (s), 3.71 (s) | $CH_3O$—C= |
| 3.90 to 4.20 (m) (7 to 8 H) | the $CH_2$'s and CH |
| 6.73 (s) | $H_4$ |
| 7.20 (d, wide) | CO—NH—CH— |
| 7.35 (dd) | $H'_5$ |
| 8.04 (d) | $H'_4$ |
| 8.37 (wd) | $H'_6$ |

-continued

| 8.94 (ws) | H'$_2$ |
| 7.72 (s), 7.80 (s) | CH = imidazole. |

EXAMPLE 30

5-[[4-[(4,5-Dihydro4-oxo1H-imidazol-2-yl)hydrazono]9,10-dimethoxy1,2,3,4,5,6-hexahydro8-benz(e)-azulenyl]oxy]pentanoic acid 300 mg of the product prepared in Stage A of Example 3 in 6 ml of ethanol is mixed at ambient temperature with 61 mg of sodium bicarbonate and 0.7 ml of ethyl bromoacetate. The solvents are evaporated off, the residue is chromatographed on silica (eluant: CH$_2$Cl$_2$-MeOH 95-5) and 139 mg of intermediate ethyl ester is obtained. 110 mg of this ester is mixed for 2 hours at ambient temperature with 1 ml of ethanol in the presence of 0.5 ml of 2N soda. After neutralization of the reaction medium using 2N hydrochloric acid, the precipitate formed is filtered off, dried and 44 mg of expected product is recovered.

NMR Spectrum (DMSO)

| ≈1.73 (m) (6 H) | central CH$_2$s and CH$_2$ in position |
| 2.30 (t) (2 H) | =C—CH$_2$ (chain) |
| 2.30 to 3.20 | =C—CH$_2$ |
| 3.73 (s), 3.75 (s) | Φ—OMe |
| 3.83 (ws) | =C—N—CH$_2$—C= |
| 4.02 (t) | Φ—O—CH$_2$ |
| 6.76 (s) | H$_4$ |
| 7.20 (ws) (1 H) } | |
| 8.28 (ws) (1 H) } | mobile H's |
| 12.04 (1 H) } | |

EXAMPLE 31

O-[9,10-Dimethoxy1,2,3,4,5,6-hexahydro4-[(4,5,6,7-tetrahydro1H-1,3-diazepin-2-yl)hydrazono]8-benz(e)azulenyl]N-[(phenylmethoxy)carbonyl]DL-homoserine 1 g of the compound prepared in Example 24 Stage A in 5 ml of butanol and 0.9 g of cyclic aminoguanidine prepared as in Preparation 11 are mixed together for 16 hours at 130° C. The solvent is evaporated off under reduced pressure, the residue is chromatographed on silica (eluant: CH$_2$Cl$_2$-MeOH 90-10) and 0.8 g of intermediate ester is obtained which is agitated at ambient temperature for one hour 30 minutes in 3 ml of methanol with 2 ml of 2N soda. After neutralizing the reaction medium using 2N hydrochloric acid and evaporation of the solvents under reduced pressure, the residue is chromato-graphed on silica (eluant: CH$_2$Cl$_2$-MeOH-NH$_4$OH 90-15-2) and 0.22 g of expected product is recovered.

EXAMPLE 32

O-[9,10-Dimethoxy1,2,3,4,5,6-hexahydro4-[(3a,4,5,6,7,7a-hexahydro1H-benzimidazol-2-yl)hydrazono]8-benz(e)azulenyl]N-[(phenylmethoxy)carbonyl]DL-homoserine The operation is carried out as in Stages B and C of Example 24 starting with 200 mg of the compound prepared in Example 24 Stage A and 176 mg of cyclic amino guanidine prepared as in Preparation 12. 102 mg of intermediate ester is recovered, 100 mg of which is used for the saponification reaction. 59 mg of expected is obtained.

Rf=0.24 (CH$_2$Cl$_2$-MeOH-NH$_4$OH 85-15-3).

Pharmaceutical Compositions

Tablets were prepared corresponding to the following formula:

| Product of Example 1 | 50 mg |
| Excipient (talc, starch, magnesium stearate) | |
| SQ for a tablet made up to | 120 mg |

Pharmacological Study of the Products of the Invention

1—Study of the Products of the Invention on the Displacement of the Binding: Vitronectin/Vitronectin Receptor ($\alpha_v\beta_3$)

Protocol:

MaxiSorp 96-well plates are coated overnight at 4° C., with 100 μl of human Vitronectin (cf Yatohgo et al. Cell., Structure and fraction 13: 281–292 (1988)) at 2 μg/ml, (Dilution in coating buffer).

The next day, the wells are emptied and the ligands (Vitronectin) are then fixed (see fixing buffer) for one hour at ambient temperature under gentle agitation.

The wells are washed six times (see washing buffer), then the following are added to each well and in this order:

40 μl of incubation buffer,

10 μl of the dilution of the product to be tested, (the products are diluted in a 50/50 mixture of DMSO-H$_2$O)

50 μl of human $\alpha_v\beta_3$ receptor (cf Pytela et al. Methods Enzymol (1987) 144:475) (dilution in incubation buffer, to be adapted according to the receptor batch and according to the ligand).

The ligand, the human $\alpha_v\beta_3$ receptor and the products to be studied are incubated for 3 hours at ambient temperature under gentle agitation.

The wells are again washed six times, then incubated for 2 hours at ambient temperature under gentle agitation, in the presence of 100 μl of anti-receptor, 4B12-HRP antibody coupled to a peroxidase (the 4B12-HRP antibody is diluted in an incubation buffer. The dilution is to be adapted according to the receptor batch).

The wells are then washed six times before the ligand-receptor binding is measured by means of a peroxidase revealer kit (TMB Microwell Peroxidase Substrate System Kirkegaard: Ref. cat. 50-76-00).

This kit contains a bottle A of substrate (3,3',5,5'-tetramethylbenzidine at 0.4 g/l) and a bottle B (H$_2$O$_2$ at 0.02% in a citrate/citric acid buffer). Extemporaneously, a volume of A is mixed with a volume of B, then the reaction mixture is distributed at a rate of 100 μl/well. The enzymatic reaction develops over 12 hours for Vitronectin/$\alpha_v\beta_3$, then its development is stopped by the addition of 100 μl of 1M phosphoric acid. The optical density is measured at 450 nm.

Buffers:

coating buffer: Carbonate 0.05 M, NaOH pH 9.6 fixing buffer: PBS containing 0.5% BSA (pH 7.4)

washing buffer: PBS containing 0.05% Tween 20 (pH 7.4)

incubation buffer:

50 mM TRIS pH 7.4

0.5% BSA 0.05% Tween 20
1 mM $MnCl_2$
50 µM $CaCl_2$
50 M $MgCl_2$
100 mM NaCl.

Expression of the Results:

The following curve is traced: the percentage of binding of the human vitronectin as a function of the logarithm of the concentration of each product tested.

For each product the $IC_{50}$ is determined according to the following formula:

$$IC_{50} = (BO+Bmin)/2$$

BO=Maximum binding in the absence of any product
Bmin=Minimum binding in the presence of the highest concentration of product.

2—Test of Mouse Calvarium

Principle

Injection of a tracer dose of $^{45}Ca$ ($CaCl_2$) to gestating female mice in order to study bone resorption by measuring the release of $^{45}Ca$ from the skullcaps of new-born mice.

Purpose

Determination of the activity of a molecule on bone resorption, ex-vivo study.

Products

1) Product to Be Tested:
Vehicle: DMSO, $H_2O$/BSA (0.1%)
Dose: Variable (10 AM in screening).

2) Reference Products:
Echistatin (ref. H-9010-BACHEM)
Vehicle: $H_2O$/BSA
Dose: 10 µM.

3) Radioactive Tracer:
$^{45}Ca$ in the form of an aqueous solution of $CaCl_2$—ref. CES3 AMERSHAM or NEZ-013 NEN.
Vehicle: Physiological serum
Dose: 25 µCi/mouse/0.4 ml Culture Medium
CMRL 1066 with phenol red (ref. 041-01535 M/GIBCO) supplemented by 0.1% BSA and penicillin/streptomycin.

Method

1) Injection of $^{45}Ca$ to Gestating Mice (OF1, Strain: Swiss)

a) Preparation of the Labelled Solution:
190 µl of the mother solution of calcium at 2 mci/ml is added to 6 ml of physiological serum.

b) Injection:
On the 17th day of gestation the mice receive 400 µl of this solution by intravenous route, that is 25 µCi/mouse.

2) Removal of the Tissue (Skullcap (Calvarium))
Six days after their birth the new-born mice are decapitated, then the head is recovered, and the skin is incised from the nape to the front. The skullcap is removed by cutting it out with scissors, and using a punch two exactly identical half-calvaria (one on the left and one on the right) are cut from the parietal bones. One will serve as the control, the other will be used to test the product to be studied.

3) "Rinsing" Phase
Each half calvarium is placed in a well of a 24-well plate, containing 1 ml of medium, on a 100 µm polyethylene and nylex support, in order to avoid all contact with the bottom of the well.

After 24 hours, the polyethylene supports carrying the calvaria are transferred into new 24-well plates containing 1 ml of fresh medium and the products to be tested or their solvents. 200 µl of medium from the first plates is removed from each well and a first count of the radioactivity is carried out (value A).

This change of medium allows all the mechanical stress associated with the removal to be eliminated.

4) "Resorption" Phase
48 hours after putting the tissues in contact with the studied products, 200 µl of medium is removed from each well and counted (value B), so as to determine the quantity of $^{45}Ca$ released from the medium during the so-called resorption phase.

The calvarium is then completely demineralized in 1 ml of 5% trichloracetic acid and after digestion, 200 µl is also removed and counted so as to determine the quantity of calcium remaining in the bone (value C). Expression of the results A % of bone resorption is calculated for each half-calvarium (each well) in the following manner:

% bone resorption=dpm B/dpm $(A+B+C) \times 100$

The sum of dpm A+B+C represents the quantity of $^{45}Ca$ incorporated in each bone part on the day of removal.

In order to measure the effect of a product, the ratio of the percentage of bone resorption of the treated well and of the corresponding control well is calculated for each point. The value found called the resorption index is comprised between 0 and 1 if the product inhibits bone resorption and is >1 if the product potentializes it. The average of the 6 indices (since there are 6 points/group) of each product is then calculated which gives one index/product. If this index is subtracted from the value 1, the inhibitory power of the product is obtained, which can be expressed as a percentage.

Furthermore a statistical test (Student T-test) is carried out by comparing point/point the individual resorption indices.

| Examples | Competition test Vn/VR (($\alpha_v\beta_3$)) binding $IC_{50}$ en µM | Mouse cavarium % inhibition at 10 µM |
| --- | --- | --- |
| EX. 2 | 0,45 | 19 |
| EX. 3 | 2,1 | — |
| EX. 6 | 0,11 | 7,5 |
| EX. 8 | 2,79 | — |
| EX. 10 | 0,8 | 8 |
| EX. 11 | 0,05 | 7 |
| EX. 22 | 2,36 | — |
| EX. 12 | 0,35 | 12 |
| EX. 14 | 0,75 | 14 |
| EX. 24 | 0,03 | 18 |
| EX. 20 | 0,079 | 11 |
| EX. 21 | 0,037 | — |
| EX. 25 | 0,013 | 26 |
| EX. 26 | 0,006 | 30 |
| EX. 27 | 0,170 | 39 |
| EX. 28 | 0,015 | 27 |
| EX. 29 | 0,028 | 18 |
| EX. 31 | 0,055 | 20 |
| EX. 32 | 0,035 | — |

What is claimed is:

1. A process for the preparation of a compound of the formula

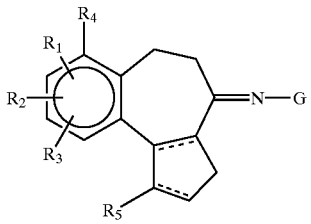
(I)

wherein R₁ is selected from the group consisting of —C≡C—A—B—COR₆, —CH=CH—A—B—COR₆, —CH₂—CH₂—A—B—COR, —OA—B—COR₆ and —CH₂—CO—A—B—COR₆, A is selected from the group consisting of a) optionally unsaturated bivalent hydrocarbyl of 1 to 12 carbon atoms and 1 to 6 heteroatoms selected from the group consisting of oxygen, sulfur and nitrogen and b) optionally unsaturated bivalent hydrocarbyl of 1 to 12 carbon atoms, B is selected from the group consisting of phenyl, —CH—Z and a single bond, Z is selected from the group consisting of hydrogen,

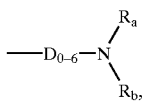

—D₀₋₆—NHSO₂R_c, —D₀₋₆—NH—CO₂R_c, —D₀₋₆—NH—COR_c, —D₀₋₆—NH—SO₂—NH—R_c, —D₀₋₆—NH—CO—NHR, —D₀₋₆—N—COOR_c, —D₀₋₆—SO₂—R_c, —D₀₋₆—COR_c and —D₀₋₆—R_c, D₀₋₆— is optionally unsaturated bivalent acyclic hydrocarbon of 0 to 6 carbon atoms, R_a, R_b and R_c are individually selected from the group consisting of hydrogen, —(CH₂)₀₋₃—Ar, —(CH₂)₀₋₃-Het and —(CH₂)₀₋₃-Alk, Ar is carbocyclic aryl of 6 to 18 carbon atoms, Het is unsaturated or saturated aromatic or non-aromatic heterocycle of 1 to 9 carbon atoms and 1 to 5 heteroatoms selected from the group consisting of oxygen, sulfur and nitrogen, Alk is selected from the group consisting of optionally unsaturated alkyl of up to 12 carbon atoms and optionally unsaturated cycloalkyl of up to 12 carbon atoms, both optionally substituted or R_a and R_b taken with the nitrogen form an unsaturated or saturated, unsubstituted or substituted aromatic or non-aromatic nitrogen heterocycle optionally having at least one other heteroatom selected from the group consisting of oxygen, sulfur and nitrogen, R₆ is selected from the group —OH, —OAlk, —OAr, —NH₂, —NH Alk and —N(Alk)₂, Alk and Ar are defined as above, R₂ and R₃ are individually selected from the group consisting of hydrogen, —OH, —OAlk and —O—(CH₂)₀₋₃—Ar, Alk and Ar defined as above or R₂ and R₃ together form —O—(CR_dR_e)_n—O—, n is an integer of 1 to 5, R_d and R_e are individually selected from the group consisting of hydrogen, alkyl of 1 to 6 carbon atoms and phenyl, R₄ is selected from the group consisting of hydrogen, halogen, —OH, —NH₂, —NO₂, —CN, —CF₃, acyl and acyloxy of an organic carboxylic acid of 1 to 12 carbon atoms, and alkyl, alkenyl, alkynyl, alkylthio, alkoxy, alkylamino, dialkylamino, dialkylaminoalkyl and dialkylaminoalkoxy of up to 6 carbon atoms, R₅ is selected from the group consisting of hydrogen, —OH, halogen, —OAlk and —O(CH₂)₀₋₃—Ar, Alk and Ar defined as above, G is selected from the group consisting of

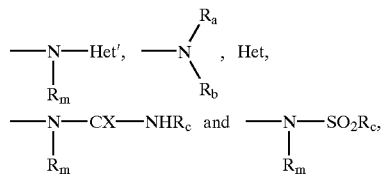

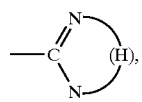

R_m is hydrogen or Alk as defined above, X is oxygen or sulfur, Het' is a heterocycle of the formula

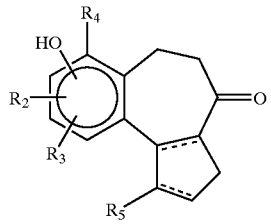

H forms the remainder of an, optionally unsaturated, mono- or bicyclic aromatic or non-aromatic heterocycle of up to 9 carbon atoms and 2 to 5 heteroatoms selected from the group consisting of oxygen, sulfur and nitrogen, the dotted lines are an optional second bond and their salts with non-toxic, pharmaceutically acceptable acids and bases and their esters comprising reacting a compound of the formula

II

wherein R₂, R₃, R₄ and R₅ are as defined above other than —OH with the compound of the formula Hal-[A]—[B]—COR₆ (F1)

in the presence of a base or with a compound of the formula

HO—[A]—[B]—COR₆ (F1')

in the presence of a phosphine and diethyl azodicarboxylate wherein Hal is halogen, B being defined as above plus —CH—NH—P, P being an amine protective group to obtain a compound of the formula (IIIa)

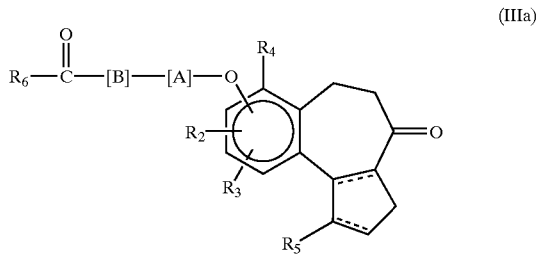

or reacting a compound of formula II with an activating agent and then with a compound of the formula

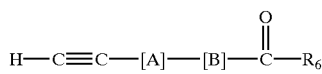 (F2)

in the presence of a catalyst to obtain a compound of the formula

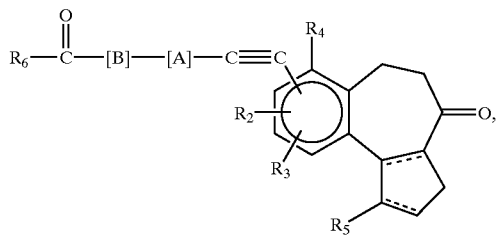 (IIIb)

reacting a compound of formula IIIa or IVb with a compound of the formula $H_2N-G$ (F3)

wherein G is defined as above to obtain the compounds of the formulae

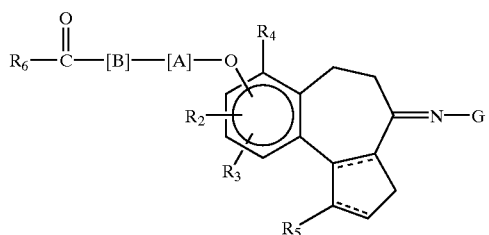 (IVa)

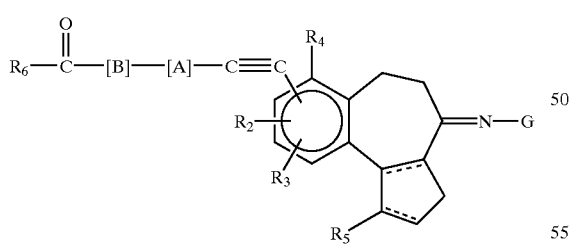 (IVb)

and subjecting the said compound to a reaction with a base or acid to change the ester to the corresponding acid.

2. The process of claim 1 wherein the compound of formula II is reacted with a compound of the formula $H_2N-G$ to obtain a compound of the formula

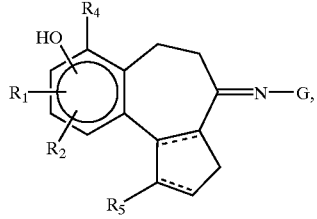 (IIIc)

protecting G, then reacting the said compound with $F_1$, F' or $F_2$ and optionally deprotecting G to obtain a compound of formula IVa and IVb.

3. The process of claim 1 wherein the compound of formula II when $R_2$, $R_3$, $R_4$ and $R_5$ are hydrogen and —OH is in position 8, 9 or 10 is prepared by reacting a compound of the formula

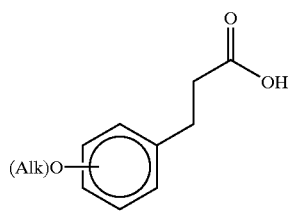 (a)

wherein —OAlk is m- or p- to the alkyl carboxylic group with a halogenation agent to form the corresponding acyl halide, reacting the latter with a compound of the formula

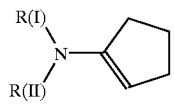 (b)

wherein $R^{(I)}$ and $R^{(II)}$ are individually alkyl of 1 to 6 carbon atoms or together with the nitrogen form a saturated or unsaturated heterocycle of 5 to 6 ring members optionally containing a second nitrogen to form a compound of the formula

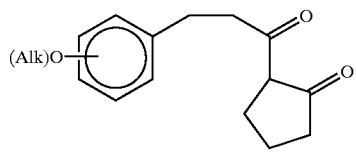 (c)

subjecting the latter to a halogenating agent to obtain a compound of the formula

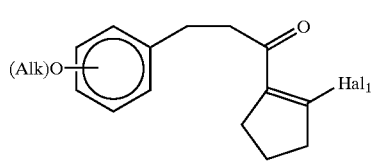 (d)

wherein $Hal_1$ is halogen, reacting the latter with a Lewis acid to from a compound of the formula

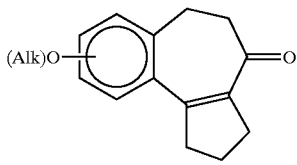
(e)

and reacting the latter with a dealkylating agent to obtain a compound of the formula

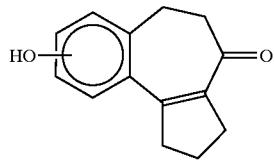
IIF

4. The process of claim 1 wherein the compound of formula II when R$_2$ is —OAlk or —O—(CH$_2$)$_{0-3}$—Ar and R$_3$, R$_4$ and R$_5$ are hydrogen and —OH and R$_2$ are in position 8, 9 or 10 is prepared by reacting a compound of the formula

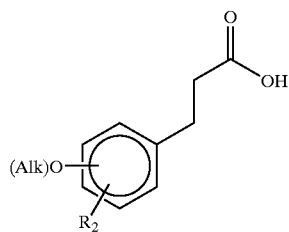
(a')

wherein R$_2$ and —OAlk are m- or p- to the alkylcarboxylic group with a halogenation agent to form the corresponding acyl halide, reacting the latter with a compound of the formula

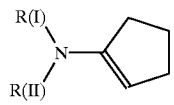
(b)

wherein R$^{(I)}$ and R$^{(II)}$ are individually alkyl of 1 to 6 carbon atoms or together with the nitrogen form a saturated or unsaturated heterocycle of 5 to 6 ring members optionally containing a second nitrogen to form a compound of the formula

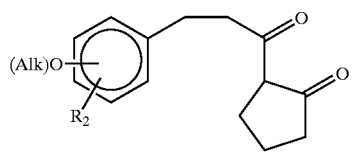
(c)

subjecting the latter to a halogenating agent to obtain a compound of the formula

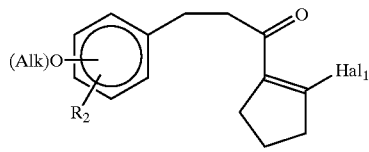
(d)

wherein Hal$_1$ is halogen, reacting the latter with a Lewis acid to form a compound of the formula

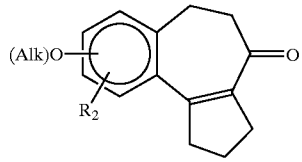
(e)

and reacting the latter with a dealkylating agent to obtain a compound of the formula

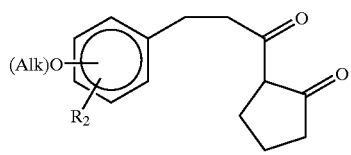
IIG

5. The process of claim 1 wherein the compound of formula II when R$_2$ and R$_3$ are —OAlk or —O—(CH$_2$)$_{0-3}$—Ar and R$_4$ and R$_5$ are hydrogen and —OH is in position 9 is formed by reacting a compound of the formula

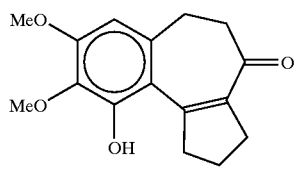
(IIA)

with an alkylation agent to obtain a compound of the formula

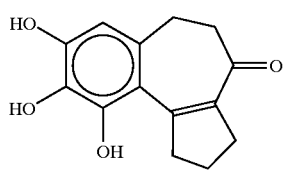
(IIB)

reacting the latter with a protecting agent of the diols in a basic medium to obtain a compound of the formula

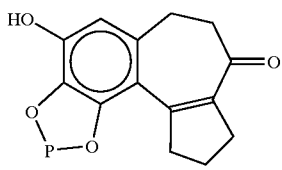
(IIC)

wherein P is the protective group and successively reacting the latter with a phenol protecting agent, a deprotecting agent for the diols, then an alkylation agent and then a phenol deprotecting agent to obtain a compound of the formula

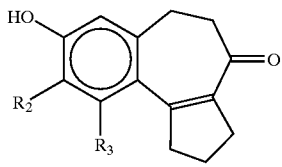
(IID)

or reacting the latter successively with a phenol protecting agent, an alkylation agent and then a phenol deprotection agent to obtain a compound of the formula

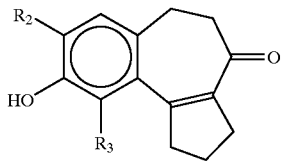
(IIE)

6. A compound having a formula selected from the group consisting of

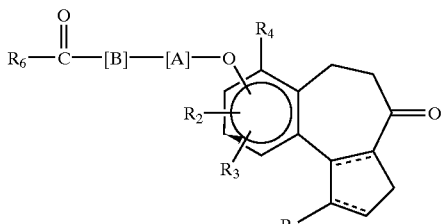
(IIIa)

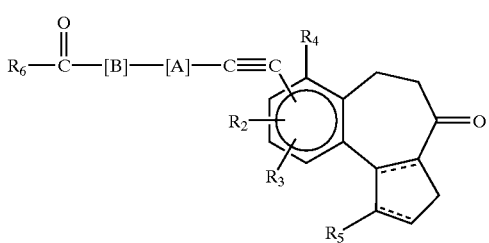
(IIIb)

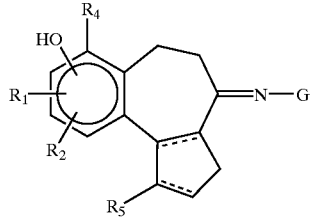
(IIIc)

and

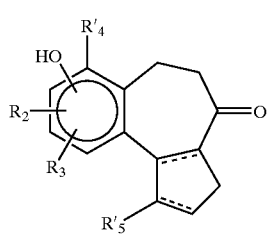
(II)

wherein $R_2$ and $R_3$ are individually selected from the group consisting of hydrogen, —OH, —OAlk and —O—$(CH_2)_{0-3}$—Ar, Alk and Ar defined as above or $R_2$ and $R_3$ together form a ring —O—$(CR_dR_e)_n$—, n is an integer of 1 to 5, $R_d$ and $R_e$ are individually selected from the group consisting of hydrogen, alkyl of 1 to 6 carbon atoms and phenyl, $R_4$ is selected from the group consisting of hydrogen, halogen, —OH, —$NH_2$, —$NO_2$, —CN, —$CF_3$, acyl and acyloxy of an organic carboxylic acid of 1 to 12 carbon atoms, and alkyl, alkenyl, alkynyl, alkylthio, alkoxy, alkylamino, dialkylamino, dialkylaminoalkyl and dialkylaminoalkoxy of up to 6 carbon atoms, $R_5$ is selected from the group consisting of hydrogen, —OH, halogen, —OAlk and —$O(CH_2)_{0-3}$—Ar, Alk and Ar defined as above, $R'_4$ and $R'_5$ are the same as $R_4$ and $R_5$ except for the hydrogen, R6 is selected from the group consisting of —OH, —OAlk, —OAr, —$NH_2$, —NHAlk and —N—$(Alk)_2$, Alk is saturated or unsaturated alkyl of up to 12 carbon atoms or saturated or unsaturated cycloalkyl of up to 12 carbon atoms, A is selected from the group consisting of a) optionally unsaturated bivalent hydrocarbyl of 1 to 12 carbon atoms and 1 to 6 heteroatoms selected from the group consisting of oxygen, sulfur and nitrogen and b) optionally unsaturated bivalent hydrocarbyl of 1 to 12 carbon atoms, B is selected from the group consisting of phenyl, —CH=Z and a single bond, Z is selected from the group consisting of hydrogen,

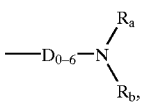

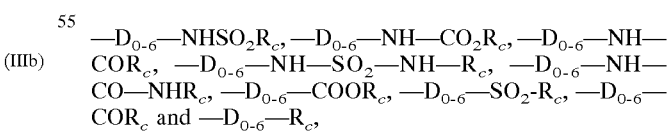

$D_{0-6}$— is optionally unsaturated bivalent acyclic hydrocarbon of 0 to 6 carbon atoms, $R_a$, $R_b$ and $R_c$ are individually selected from the group consisting of hydrogen, —$(CH_2)_{0-3}$—Ar, —$(CH_2)_{0-3}$-Het and —$(CH_2)_{0-3}$-Alk, Ar, is carbocyclic aryl of 6 to 18 carbon atoms, Het is optionally unsaturated aromatic and non-aromatic heterocycle of 1 to 9 carbon atoms and 1 to 5 heteroatoms selected from the group consisting of oxygen, sulfur and nitrogen is selected from the group consisting of

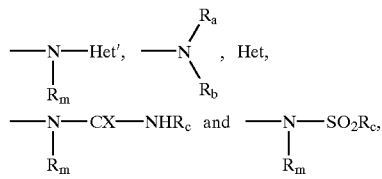

$R_m$ is hydrogen or Alk as defined above, X is oxygen or sulfur, Het' is a heterocycle of the formula

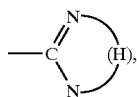

H forms the remainder of an optionally unsaturated, mono- or bicyclic aromatic or non-aromatic heterocycle of up to 9 carbon atoms and 2 to 5 heteroatoms selected from the group consisting of oxygen, sulfur and nitrogen, the dotted lines are an optional second bond.

* * * * *